(12) United States Patent
Rhodes

(10) Patent No.: US 8,160,899 B2
(45) Date of Patent: Apr. 17, 2012

(54) KNOWLEDGE BASED ELECTRONIC CLINICAL RECORD FOR DENTISTRY

(76) Inventor: Paul Rhodes, Oakland, CA (US)

( * ) Notice: Subject to any disclaimer, the term of this patent is extended or adjusted under 35 U.S.C. 154(b) by 658 days.

(21) Appl. No.: 12/023,084

(22) Filed: Jan. 31, 2008

(65) Prior Publication Data

US 2009/0198514 A1    Aug. 6, 2009

(51) Int. Cl.
*G06Q 10/00*    (2006.01)
(52) U.S. Cl. .................................. 705/3; 705/2
(58) Field of Classification Search ........................ 705/2
See application file for complete search history.

(56) References Cited

U.S. PATENT DOCUMENTS

| | | | |
|---|---|---|---|
| 4,889,132 A * | 12/1989 | Hutcheson et al. ........... | 600/493 |
| 5,592,945 A | 1/1997 | Fiedler | |
| 5,823,948 A | 10/1998 | Ross | |
| 6,438,533 B1 | 8/2002 | Spackman et al. | |
| 6,581,038 B1 | 6/2003 | Mahran | |
| 6,684,276 B2 | 1/2004 | Walker et al. | |
| 6,736,776 B2 * | 5/2004 | Miles ........................... | 600/300 |
| 6,915,265 B1 | 7/2005 | Johnson | |
| 7,154,397 B2 * | 12/2006 | Zerhusen et al. ........... | 340/573.1 |
| 7,156,655 B2 * | 1/2007 | Sachdeva et al. ............... | 433/24 |
| 7,234,937 B2 * | 6/2007 | Sachdeva et al. ............... | 433/24 |
| 7,717,708 B2 * | 5/2010 | Sachdeva et al. ............... | 433/24 |
| 7,778,851 B2 * | 8/2010 | Schoenberg et al. ............. | 705/3 |
| 7,831,450 B2 * | 11/2010 | Schoenberg et al. ............. | 705/3 |
| 7,899,683 B2 * | 3/2011 | Schoenberg et al. ............. | 705/2 |
| 2007/0185390 A1 * | 8/2007 | Perkins et al. ................. | 600/300 |

OTHER PUBLICATIONS

DecisionBase, Inc., TiME for Denistry User's Manual, Premium Edition for Periodontics, 1995-2001.*
Declaration of Paul Rhodes, and Exhibits.
User Manual TiME version 2.3 (4-65 pages), Exhibit A to Rhodes Declaration.

* cited by examiner

*Primary Examiner* — Robert Morgan
*Assistant Examiner* — Michael Fuelling
(74) *Attorney, Agent, or Firm* — Barnes & Thornburg LLP

(57) ABSTRACT

The present invention relates to an electronic records management system. More specifically, the present invention is a comprehensive knowledge based clinical records management solution that encompasses the need for accurate records, while reducing the time and effort required to enter complete and accurate information.

13 Claims, 26 Drawing Sheets

FIGURE 2

```
GeneralHealthSummary                          🗗 ⎘ ×
07/11/06:
Last Physical Exam: 10/06
Allergic to: Latex
Current Medications:
    ASA 81 mg/day
    multi-vitamins
    Atenalol
Significant Medical Conditions
    Hypertension x 6 yrs, controlled by meds
Review of Systems:
    No contra-indications to planned care
```

Ralationships between Patient-Session and Various Categories of Data

Items are selected from a Category List. The selected items are incorporated into a specific date-related session which is linked to a specific patient

Paul Revere, DDS, MS
*Reconstructive Implant, Periodontal and Orofacial Surgery*
12 Backwater Bay, Boston, MA 02102  ph: 508-222-1111

01/12/1776

Dr. Jonathon Z. Smith
123 Main St
Indianville, MA 02032

Report of treatment performed on John Adams

Dear John:

Today, John Adams was seen for treatment. Below is a summary of what was encountered and performed:
- Indications for procedure
   - Lack of connective tissue attachment to the root surface
   - Significant root exposure with associated root sensitivity
- Goals of the procedure
   - Cover the exposed root surface to reduce risk of caries
   - Cover exposed root surface to treat root sensitivity
- Root preparation included
   - root flattening with - finishing burs
   - root surfaces were polished with fine pumice
   - root conditioning using - citric acid was applied for 30 seconds
- Graft tissue consisted of:
   - donor site: the right side of the palate; graft thickness: 1.5 to 2.5mm (medium)
- Graft and flap positioning
   - the graft material was placed on periosteal bed and root surface - 5-6
   - Flap positioning: coronally positioned to partially cover the graft
- Intra-operative Findings:
   - thin alveolar housing with dehiscence of the root of #6
- Suturing & Coverage :
   - sutured by continuous rolling suturing with polypropylene (8-0)
- Hemostasis attained by: appplication of external pressure.
- Donor Site Management:
   - sutured by continuous horizontal mattress suturing with Monocryl (5-0)
- Surgical site coverage: a surgical stent.
- Local anesthetics administered:
   - Lidocaine 2% 1:100,000 epi 2 carp (72mg). Pre-discharge Summary
- The procedure went as planned without complications
- Vital signs are within normal limits Bleeding is under control
- The patient is comfortable and ready to dismiss Please give me a call or jot me a note if you have any questions or comments.

Sincerely yours,

Paul Revere, DDS, MS

FIGURE 17

KNOWLEDGE BASED ELECTRONIC CLINICAL RECORD FOR DENTISTRY

BACKGROUND OF THE INVENTION

1. Field of the Invention

The present invention relates to an electronic records management system. More specifically, the invention relates to electronic records management systems generally in the field of medical records, and has aspects that specifically relate to dental medical records.

2. Description of the Related Art

The World Health Organization defines Dentistry as 'the science and art of preventing, diagnosing and treating diseases, injuries and malformations of the teeth, jaws and mouth.' Problems with teeth and gums have troubled humans for thousands of years. Ancient Egyptian medical texts, dating back to 3500 BC, refer to toothaches. Hesi-Re, an Egyptian who lived around 3000 BC, is the earliest dentist known by name. Organized dentistry began when the world's first dental school, the Baltimore College of Dental Surgery, opened in Baltimore, Md. in 1840.

The first business computer was used for the first time in 1951 to take the United States census. By 1962, there were over 40,000 business computers in the United States. In just one more year, that number doubled. Since that time businesses have utilized computers in a variety of ways. One major computer use for many businesses is records management. Obviously, keeping complete and accurate records and maintaining them securely is vital to all medical professionals. Over 160 dental practices lost all of their physical patient records as a result of Hurricane Katrina. This loss could have been prevented by offsite secure storage of electronic copies of records. Electronic records management has eclipsed physical records management as the preferred option for most practitioners. Ever-evolving compliance regulations and statutes have also increased interest in electronic records management systems among businesses including dental practices. Dental practitioners constantly strive to make their offices more efficient, saving time, effort and money. Having a comprehensive electronic system in place where copious patient records can be maintained and easily accessed makes the practice run more efficiently and helps provide patients the best possible care.

According to the American Dental Association (ADA), the primary professional organization of dentists (American Dental Association and ADA are registered trademarks of the American Dental Association Corporation of Chicago, Ill.), there are more than 175,000 licensed dentists practicing in the United States today. Nine out of ten are in private practice. Making accurate and complete record entries is a crucial area of professional responsibility. A record entry must be made for every patient interaction that occurs, from a missed appointment to a final cementation and including all relevant data regarding each patient's treatment. Dental practitioners are constantly striving for ways to achieve higher quality, more efficient communication, reduced administrative time and costs, and to reduce the burden of keeping up with patient charts, dictation and correspondence. Many dentists are converting to digital recordkeeping in their quest to save time, paper and money while maintaining accuracy.

There are many important reasons for keeping thorough, accurate records. First, it helps facilitate better patient care. Referring to descriptions of prior patient care helps the dentist evaluate the effectiveness of care. Second, a patient may be treated in several different clinics. To ensure the smooth transition of a patient from clinic to clinic, information must be easily transmittable. The patient record is often the sole source of vital facts concerning patient treatment status. Third, the patient record is the mechanism by which insurance claims are filled out, itemized statements prepared, and charges are reviewed for accuracy. In order to determine charges accurately, the details of each procedure must be well documented. Fourth, the efficient use of the time of all involved in patient care is yet another important reason for making complete and legible record entries.

Previous versions of the records management system detailed below reduced the effort required in creating patient charts by utilizing a glossary of medical and/or dental specific terms, organized in an expandable/collapsible hierarchical tree. The user could select a term or branch node, with each branch node being expandable to reveal further terms or nodes for selection. The user could then select a desired term without further data entry. While this hierarchical structure provided benefits for the dental practitioner, the inventor of this system continued development of the system to further enhance the interaction with the dental practitioner.

SUMMARY OF THE INVENTION

The present invention is a clinical records management system that encompasses the need for comprehensive, accurate records, while reducing the time and effort required to record complete and accurate information. While the application uses terminology common to dentistry, the organization of terminology into procedure specific digital forms is unique and constitutes a domain specific knowledge base. This organization constitutes algorithms which are also domain specific knowledge. Additionally, making selections from these forms and having the application automatically generate from that the notes which constitute the clinical patient records The present invention employs a configurable computer graphical user interfaces (GUI) to effectuate an efficient and smooth flow of data entry which can then be viewed in various ways or converted into a variety of documents for sharing patient clinical information with other treating healthcare providers. Additionally, the application knowledge base includes a variety of documents to aid in communications with patients: procedure specific informed consents, procedure specific pre-operative and post-operative patient instructions and instructions for taking specific medications including descriptions of possible side effects, warnings and risks. There are at least four different aspects of the present invention and each is discussed in detail below in relation to embodiments of the invention.

One aspect of the present invention is the Main User Interface (UI). The Main UI consists of eight interrelated, editable areas. The Main UI's opening view consists of a thumbnail view of several categories of data, along with a patient identifier data area and a list of prior sessions (entries) area. The thumbnail views are 'window-panes' each of which can be expanded to fill the entire main window so associated data can be more easily viewed and/or edited. The categories may include a dental chart area, planned treatment area, a list of prior documents generated area, a list of patient alerts & modifiers area, a summary of the patient's general health area and a medications prescribed area. These categories of information to be viewed in this opening UI may be configured by the end-user.

Another aspect of the present invention relates to Procedure Specific Forms which provide the user with the ability to create chart entries by selecting items from a form instead of typing. These forms are present in several embodiments of the invention. The user makes selections from checkboxes, dropdown lists and multiple choice lists resulting in a compound template made up of the specific selected items. The application then filters the entire procedure-specific form for those items selected by the user and creates a document describing what occurred during a particular patient session. This component allows the user to easily generate readable output based on user selections that is then copied to a separate word processing program and converted into an outline formatted document, thus reducing the number of keystrokes (and mouse clicks) necessary to create the desired output.

A further aspect of the present invention is the mechanism for building 'Procedure Specific Template/Forms. 'Template/Forms' are electronic (digital) 'forms' that contain multiple Data Fields specific to a particular procedure or patient-related event. Using a domain specific knowledge base, a user can create these electronic forms each of which contains all areas of information pertinent to the procedure being described as well as all of the possible iterations for each of the steps in the procedure. These complex forms are subdivided into sections by 'Tabs' (pages). Selection is made by either checking items associated with Checkboxes, Drop-Down List boxes or Multiple Choice List boxes, as well as a variety of custom controls.

Another aspect of the present invention relates to the Anesthesia Record. The standard of care for patients receiving conscious sedation, deep sedation or general anesthesia in a dental environment calls for the documentation of drugs, gases and other agents administered as well as the patient's vital signs and oxygen saturation during anesthesia. While local anesthesia is the most common form of pain control used by general dentists, sedation, analgesia and general anesthesia are taught in most dental specialty residencies and are regularly used by dental specialists in practice. Therefore, an anesthesia record is a significant component of an electronic dental patient record. The anesthesia record in this application is unique in that it contains areas of information not included in other dental EMR's: pre-anesthesia physical evaluation, validation of equipment operation and supplies of gases, a description of the method of administration, the airway management, the agents administered, the vital signs and the pre-discharge status of the patient. All of these elements are important to assuring a safe and conservative anesthesia experience for the patient. Furthermore, the depth of documentation affords the practitioner of better risk management. Additionally, the entry of vital signs (blood pressure, pulse, oxygen saturation of the blood) may be automatically recorded directly from monitoring devices thus eliminating errors in entry.

Another aspect of the present invention relates to a unique set of data and display (UI) known as the 'PerioProfile.' This UI allows for the collection and display of more elements of data relevant to the extent of disease as well as evidence of current disease (inflammatory) activity. In addition to the data values collected and included on a traditional periodontal chart, the PerioProfile can collect and simultaneously display data on signs of inflammatory activity by calculating and displaying indices for 'Bleeding' and 'Exudate' activity; collect and display data on a patient's plaque control effectiveness (a 'Plaque Score'), and other strategic items of dental and periodontal morphologic data pertinent to periodontal evaluation. Alphanumeric data is displayed in a 'spreadsheet' format so that data for a specific site can be readily reviewed by scanning down a vertical column. Additionally, this same data is displayed graphically around graphics of individual teeth and implants and can include an overlay of periodontal supporting bone and gingiva to show the relationship between data items and these anatomic structures. This display of graphical periodontal data can be viewed with overlays of supporting bone and or gingiva. This comprehensive spreadsheet and graphical view of periodontal data including relationships with alveolar bone and gingiva is a unique design feature of this application.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIG. 2 is a screenshot view of the main graphical user interface of one embodiment of the present invention.

FIGS. 7A and 7B are screenshot window pane views of the General Health Summary area of FIG. 2.

FIGS. 9A-9D are screenshot window pane views of the Anesthesia Record page according to another embodiment of the present invention.

FIGS. 13A and 13B are screenshot views of a periodontal charting input and display relating to the Dental Chart of FIG. 4 according to one embodiment of the present invention.

FIG. 15 is a screenshot view of a Connective Tissue Graph session window according to one embodiment of the present invention.

FIG. 16 is a screenshot view of a Dentoalveolar Examination window pane according to one embodiment of the present invention.

FIG. 17 is a plan view of a Reconstructive Implant, Periodontal and Orofacial Surgery bullet point report letter generated by one embodiment of the present invention.

Figure 1:
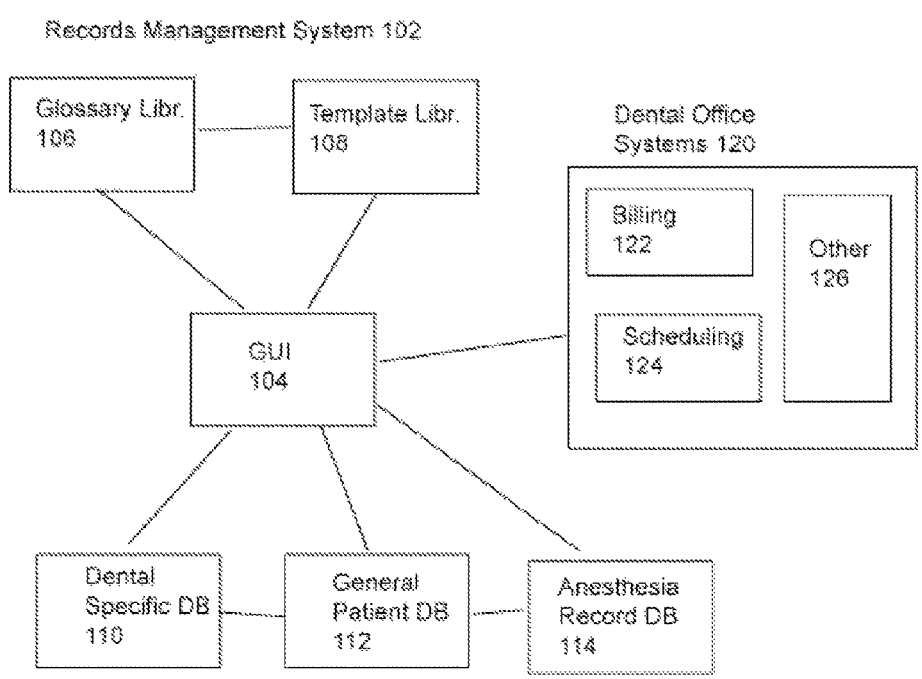
FIG. 1 is a schematic diagrammatic view of the clinical records management system according to one embodiment of the present invention.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiment disclosed below is not intended to be exhaustive or limit the invention to the precise form disclosed in the following detailed description. Rather, the embodiment is chosen and described so that others skilled in the art may utilize its teachings.

The detailed descriptions which follow are presented in part in terms of algorithms and symbolic representations of operations on data bits within a computer memory representing alphanumeric characters or other information. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, symbols, characters, display data, terms, numbers, or the like. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory; rather they represent specific electronic structural elements which impart a physical organization on the information stored in memory. More than mere abstraction, the data structures are specific electrical or magnetic structural elements in memory which simultaneously represent complex data accurately and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical signals.

The present invention also relates to an apparatus for performing these operations. This apparatus may be specifically constructed for the required purposes or it may comprise a general-purpose computer as selectively activated or reconfigured by a computer program stored in the computer. The algorithms presented herein are not inherently related to any particular computer or other apparatus. In particular, various general-purpose machines may be used with programs written in accordance with the teachings herein, or it may prove more convenient to construct more specialized apparatus to perform the required method steps. The required structure for a variety of these machines will appear from the description below.

The present invention deals with 'object-oriented' software, and particularly with an 'object-oriented' operating system. The 'object-oriented' software is organized into 'objects', each comprising a block of computer instructions describing various procedures ('methods') to be performed in response to 'messages' sent to the object or 'events' which occur with the object. Such operations include, for example, the manipulation of variables, the activation of an object by an external event, and the transmission of one or more messages to other objects.

Messages are sent and received between objects having certain functions and knowledge to carry out processes. Messages are generated in response to user instructions, for example, by a user activating an icon with a 'mouse' pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a 'circle' on a display may inherit functions and knowledge from another object for drawing a 'shape' on a display.

A programmer 'programs' in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system can be modeled with an object, the behavior of each component being simulated by the methods of its corresponding object, and the interactions between components being simulated by messages transmitted between objects. Objects may also be invoked recursively, allowing for multiple applications of an objects methods until a condition is satisfied. Such recursive techniques may be the most efficient way to programmatically achieve a desired result.

An operator may stimulate a collection of interrelated objects comprising an object-oriented program by sending a message to one of the objects. The receipt of the message may cause the object to respond by carrying out predetermined functions which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are 'invisible' to an observer since only a relatively few steps in a program typically produce an observable computer output.

In the following description, several terms which are used frequently have specialized meanings in the present context. The term 'object' relates to a set of computer instructions and associated data which can be activated directly or indirectly by the user. The terms 'windowing environment', 'running in windows', and 'object oriented operating system' are used to denote a computer user interface in which information is manipulated and displayed on a video display such as within bounded regions on a raster scanned video display. The terms 'network', 'local area network', 'LAN', 'wide area network', or 'WAN' mean two or more computers which are connected in such a manner that messages may be transmitted between the computers. In such computer networks, typically one or more computers operate as a 'server', a computer with large storage devices such as hard disk drives and communication hardware to operate peripheral devices such as printers or modems. Other computers, termed 'workstations', provide a user interface so that users of computer networks can access the network resources, such as shared data files, common peripheral devices, and inter-workstation communication. The computers have at least one processor for executing machine instructions, and memory for storing instructions and other information. Many combinations of processing circuitry and information storing equipment are known by those of ordinary skill in these arts. A processor may be a microprocessor, a digital signal processor ('DSP'), a central processing unit ('CPU'), or other circuit or equivalent capable of interpreting instructions or performing logical actions on information. Memory includes both volatile and non-volatile memory, including temporary and cache, in electronic, magnetic, optical, printed, or other format used to store information. Users activate computer programs or network resources to create 'processes' which include both the general operation of the computer program along with specific operating characteristics determined by input variables and its environment.

The terms 'desktop', 'personal desktop facility', and 'PDF' mean a specific user interface which presents a menu or display of objects with associated settings for the user associated with the desktop, personal desktop facility, or PDF. When the PDF accesses a network resource, which typically requires an application program to execute on the remote server, the PDF calls an Application Program Interface, or 'API', to allow the user to provide commands to the network resource and observe any output. The term 'Browser' refers to a program which is not necessarily apparent to the user, but which is responsible for transmitting messages between the PDF and the network server and for displaying and interacting with the network user. Browsers are designed to utilize a communications protocol for transmission of text and graphic information over a worldwide network of computers, namely the 'World Wide Web' or simply the 'Web'. Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information which is formatted in a Standard Generalized Markup Language ('SGML') or a HyperText Markup Language ('HTML'), both being scripting languages which embed non-visual codes in a text document through the use of special ASCII text codes. Files in these formats may be easily transmitted across computer networks using a hypertext transfer protocol ('HTTP') or a secure HTTP ('SHTTP'), including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ('XML') file, with XML files being capable of use with several Document Type Definitions ('DTD') and thus more general in nature than SGML or HTML. The XML file may be analogized to an object, as the data and the stylesheet formatting are separately contained (formatting may be thought of as methods of displaying information, thus an XML file has data and an associated method).

The terms 'personal digital assistant' or 'PDA', as defined above, means any handheld, mobile device that combines computing, telephone, fax, e-mail and networking features. The terms 'wireless wide area network' or 'WWAN' mean a wireless network that serves as the medium for the transmission of data between a handheld device and a computer. The term 'synchronization' means the exchanging of information between a handheld device and a desktop computer either via wires or wirelessly. Synchronization ensures that the data on both the handheld device and the desktop computer are identical.

In wireless wide area networks, communication primarily occurs through the transmission of radio signals over analog, digital cellular, or personal communications service ('PCS') networks. Signals may also be transmitted through microwaves and other electromagnetic waves. At the present time, most wireless data communication takes place across cellular systems using second generation technology such as code-division multiple access ('CDMA'), time division multiple access ('TDMA'), the Global System for Mobile Communications ('GSM'), personal digital cellular ('PDC'), or through packet-data technology over analog systems such as cellular digital packet data (CDPD') used on the Advance Mobile Phone Service ('AMPS').

The terms 'wireless application protocol' or 'WAP' mean a universal specification to facilitate the delivery and presentation of web-based data on handheld and mobile devices with small user interfaces.

The term 'Session' means a specific patient related encounter. Some sessions will be related to a patient visit to the dentist's office. Others sessions will be to document something else related to the patient (for example, phoned in a prescription, phone call to the patient, documents mailed to the patient, etc.).

The term 'Procedure' relates to a specific patient related event such as a Periodontal Exam or an Implant Surgery. A procedure is based on a 'Type' and a 'Sub-specialty.'

The term 'Type' means the type of process being performed and documented during a particular patient session. For example, Exam, Treatment, Progress, Outcomes, etc.

The term 'Template' means an electronic (digital) 'form' which contains multiple Data Fields specific to a particular procedure or process. Templates are based on a specific combination of a 'Type' and a 'Sub-specialty.' A Template may be an editable document having certain information already present and predefined sections for data entry, or may be a rule based document generator as described in more detail below.

The terms 'Record' and 'Chart' relate to a patient's clinical documentation (i.e., the clinical record or the clinical chart).

The present invention generally involves a knowledge based clinical records management solution which employs a configurable computer graphical user interface (GUI) to effectuate an efficient and smooth flow of data from the end-user to the clinical records. The embodiments of the present invention provide for the creation, management, use and sharing of clinical patient information in a dental practice, although many aspects of the present invention are applicable in the general medical field. There are at least four aspects of the present invention and each is discussed in detail below in discussions of the associated embodiments of the invention. FIG. 1 depicts a schematic representation of clinical records management system 102. Main User Interface (UI) 104 is capable of obtaining and displaying patient-related from a plurality of databases. Main UI also accesses non-patient related data that is needed to operate a Dental Office. Dental Office Systems 130 may include Billing 132, Scheduling 134 and other systems 136 that may be used in the office of a dental practice. Records Management System 102 includes Main UI 104 which reads and updates patient data in Dental Specific database 120, General Patient database 122 and Anesthesia Record database 124. User input is facilitated and made easier using Knowledge Base 108, discussed in detail below. Records Management System 102 may be implemented as a stand alone program, including all the programming necessary to interact with databases 120, 122, and 124. Alternatively, Records Management System 102 may interact with existing database programs that manage databases 120, 122, and 124.

Figure 2:
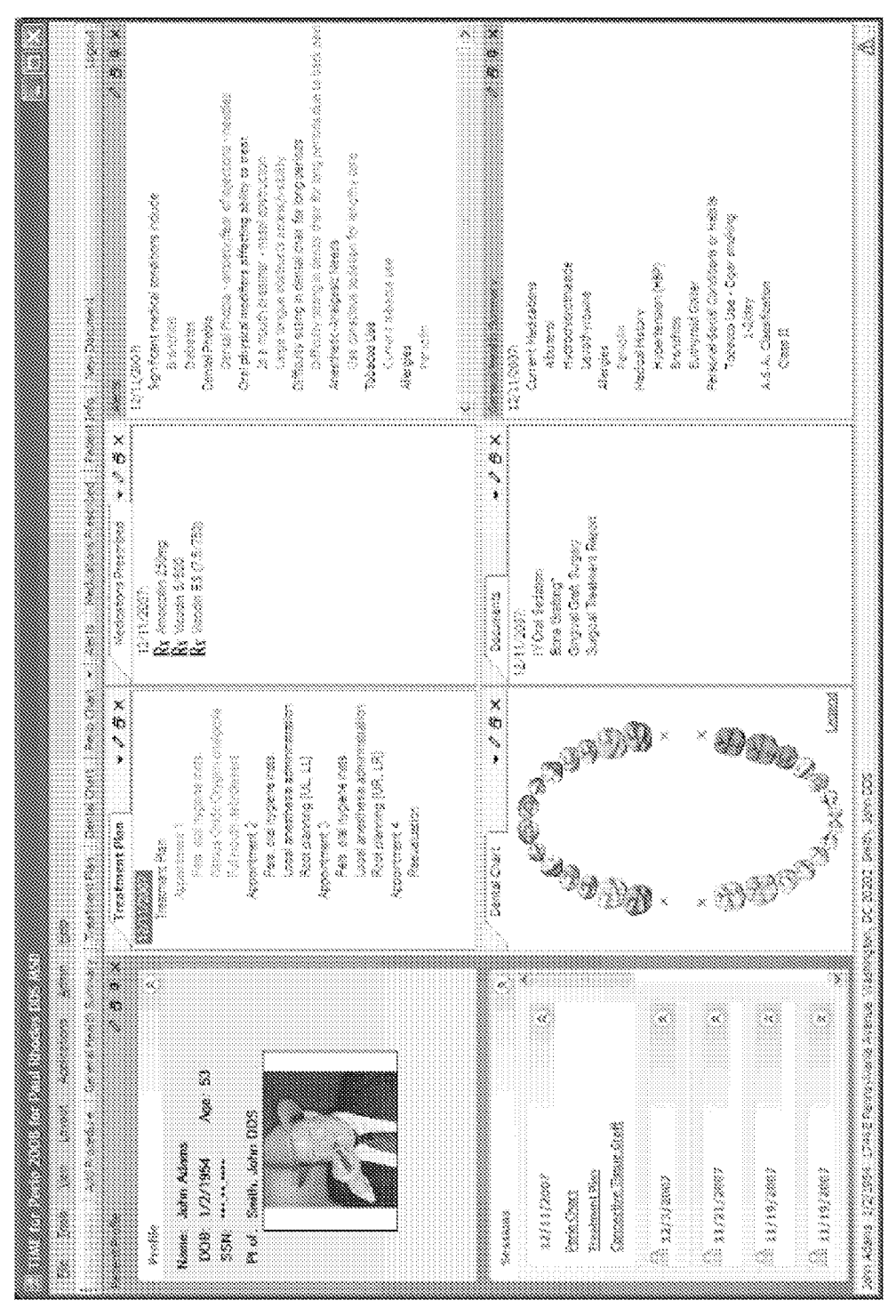
Figure 14:
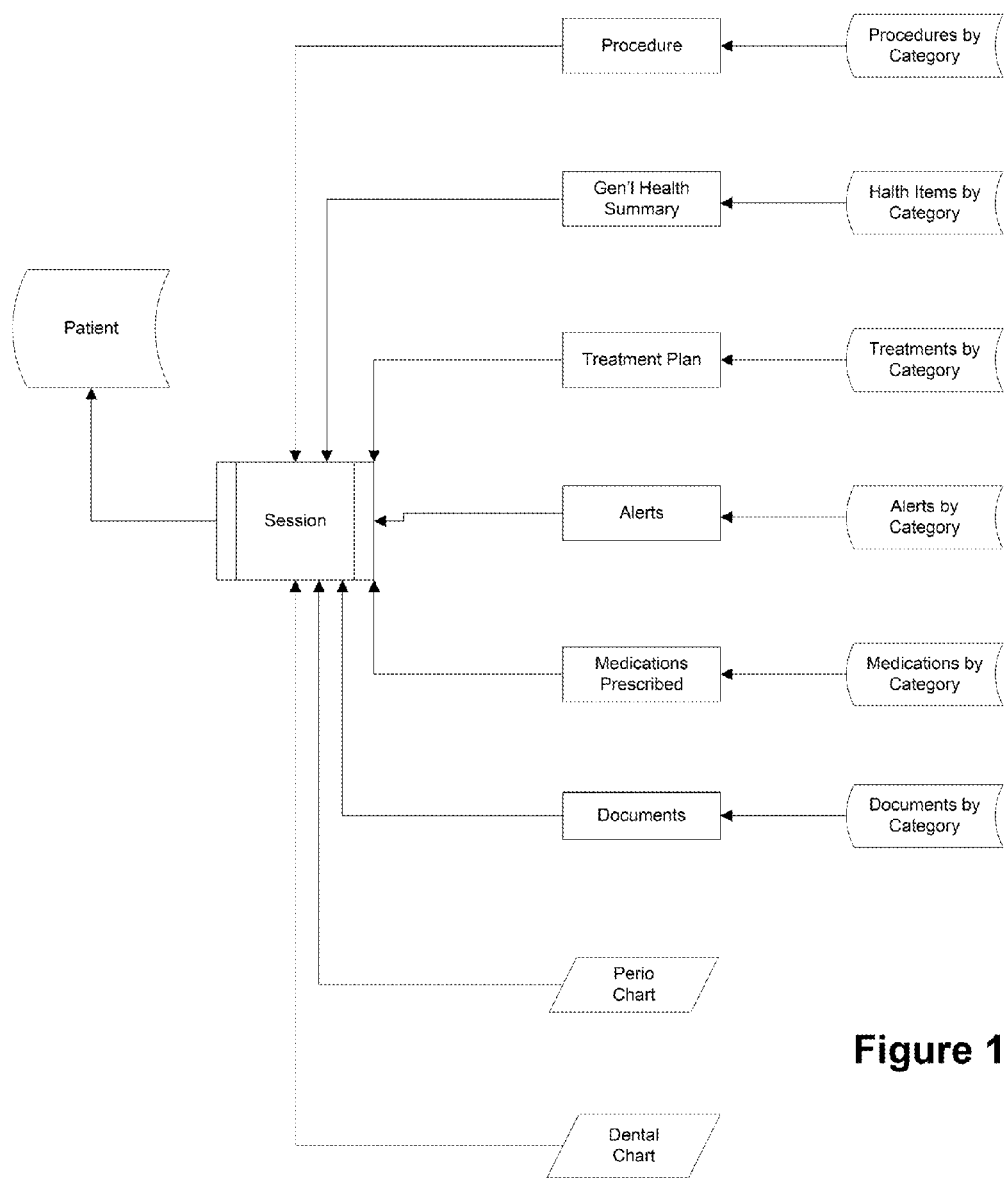
FIG. 14 is a schematic relational diagram of the session entries of FIG. 3.

One embodiment of the present invention includes Main UI 104 which is depicted in FIG. 2. Main UI 104 is divided into vertical columns on the computer screen which includes, in this exemplary embodiment, an upper box in the left most column having patient ID information. Below that is a window pane which has a list of sessions for the patient, as sessions are described in greater detail with regards to FIGS. 3 and 14. To the right of this is the 'Main Window' for the application. These thumbnail views are 'window-panes,' each of which can be expanded to fill the entire main window so that they can be more easily viewed or read. The Main UI, in this exemplary embodiment, consists of eight areas. The exact number of areas, and the selection and arrangement of such areas, may be modified for accommodating various desired data displays and/or hardware configurations of the displaying device. For example, additional data viewing may be provided depending on the amount and character of patient data maintained by records management system 102. Alternatively, the shape and size of the areas may be adapted to smaller screens generally available on hand-held devices or to larger display screen than conventionally used in a dental practitioner's office.

Figure 3:
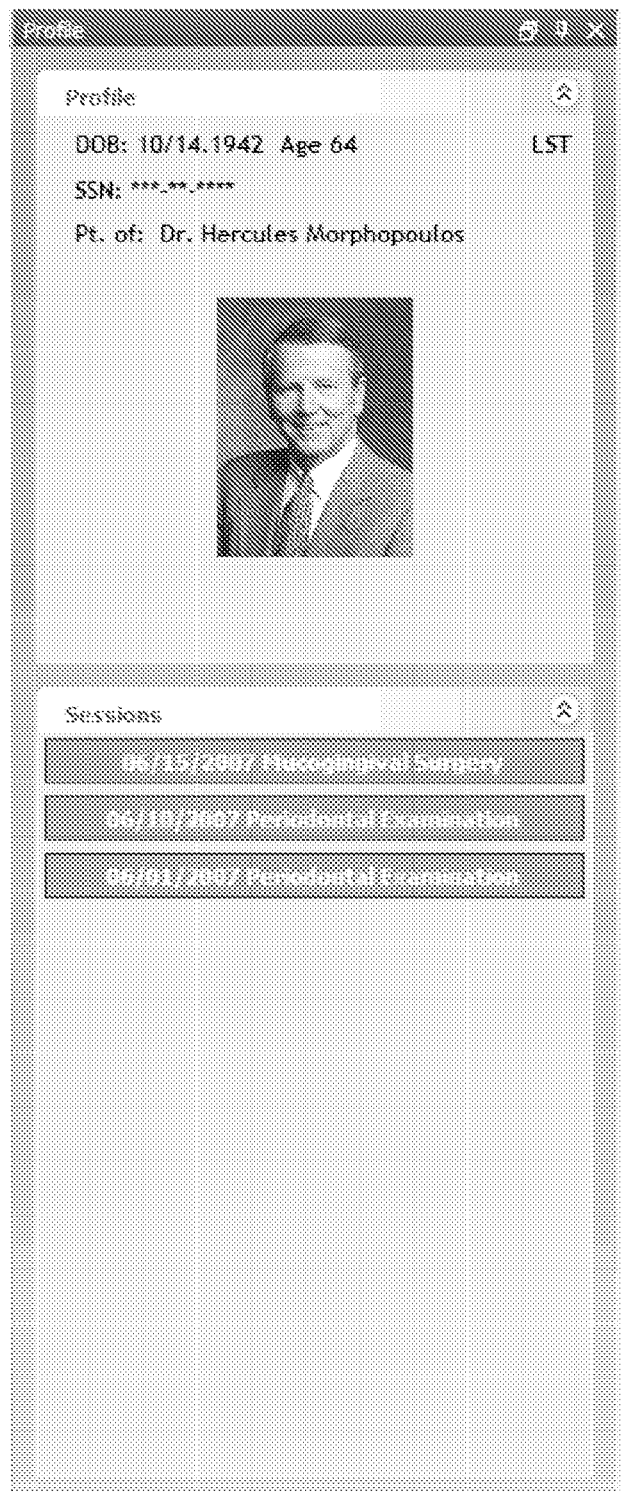
FIG. 3 is a screenshot window pane view of the Patient Identifier and Sessions areas of FIG. 2.

Patient identifier area 1 comprises, in the exemplary embodiment, patient-related data as depicted more particularly in FIG. 3. The data may include, but is not limited to, full legal name, address, other contact information (e.g., phone, mobile phone, instant messaging, e-mail), date of birth, age in years, primary health care provider (dentist and/or doctor), social security number (SSN), health insurance information (policy issuer and policy number), name of the patient's primary care dentist, and a photo or portrait of the patient. For Health Insurance Portability and Accountability Act (HIPAA) compliance, the SSN is not readily viewable on the screen and only displays in a 'popup' when the mouse 'hovers' over the 'SSN' icon. The exact information displayed may be configured by the user for personal or office preferences and procedures.

Shown in FIG. 2, Sessions List area 2 includes a list of prior data entries relating to treatment sessions of the patient prior to any current windows. FIG. 3 shows this in greater detail, with the lower portion of the window pane as including a list of sessions. Each session is a collection of information about a particular patient visit. The selection of a particular session results in the population of the other window panes of Main UI 104. This allows the practitioner/user to view in one screen a summary of the relevant patient data available electronically, and the practitioner/user may drill down any of the other window panes (as described in greater detail below) to obtain the full data from any of these summaries. Further, the practitioner/user may initiate a new session. When a new session is initiated, the data record or object associated with the new session inherits the information from the immediately prior session, allowing the practitioner/user to avoid having to enter duplicative data, so that only the entry of new data and/or the deletion of old data is required. In the exemplary embodiment, only session information in the current session may be edited and prior session information is available in read-only mode. However, it is possible to configure the software to provide permission based editing features, so that a user and/or super-user may be able to modify certain prior session data.

Figure 4:
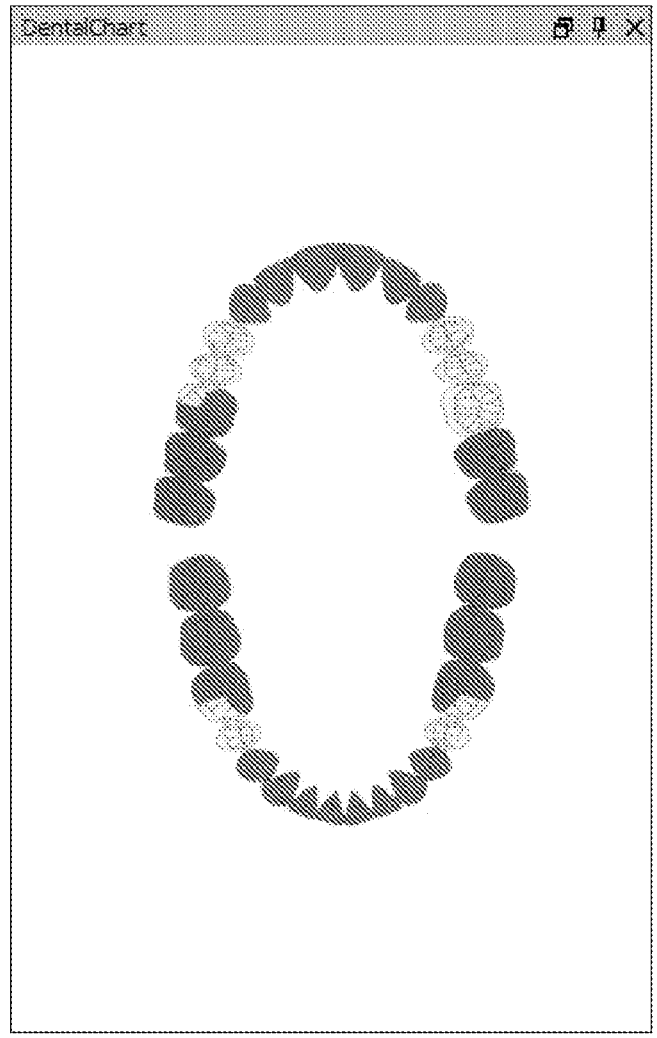
FIG. 4 is a screenshot window pane view of the Dental Chart area of FIG. 2.
Figure 5:
FIG. 5 is a screenshot window pane view of the Planned Treatment area of FIG. 2.

Dental Chart area 3, shown in FIG. 2 and particularly in FIG. 4, includes an occlusal view of the teeth in the upper (maxillary) and lower (mandibular) arches (jaws). Occlusal relates to the grinding or biting surface of a tooth. Dental chart area 3 makes use of color-coding to depict missing teeth, the presence of crowns, implants and other dental treatments. Dental Chart area 3 gives the end-user a quick, yet informative way of viewing the patient's teeth. In addition, more detailed periodontal charting may be invoked from this area 3 as described in greater detail below in the discussion of FIGS. 12 and 13.

Treatment Planned area 4, depicted in FIG. 2 and particularly in FIG. 4, lists treatments that are planned for the patient and may make use of color-coding to show which treatments had been carried out and which treatments still need to be carried out. Color-coding allows the data to be presented in a way that allows the end-user an easy way to quickly determine what planned treatments have been carried out and which are still needed. Billing codes and descriptions of all parts of the treatment plan that are billable items are passed to Dental Office Systems 130. This eliminates duplicate entries and the possibility of errors.

Depicted in FIG. 2, Treatment area 5 includes a list of prior patient encounters that had been documented in the patient's clinical record (treatments and other patient interaction events relevant to a treatment plan). The display, in this exemplary embodiment, is by date of the treatment. Double-clicking on any treatment date brings up the details of that treatment in either of the following ways: (a) the narrative notes as displayed below in section; or (b) the form used to enter notes allowing modification of the notes. The display, in another embodiment, may be by date and title of the treatment.

Figure 6:
FIG. 6 is a screenshot window pane view of the Alerts & Modifiers area of FIG. 2.

Alerts & Modifiers area 6 of FIG. 2 is shown more particularly in FIG. 6. A&M area 6 includes listings of the current significant risk factors or modifiers that had been added to the patient's record that should be 'flagged' and brought to the practitioner's attention because they were associated with highlighted risk or required specific needs when examining or treating the patient. The contents of A&M 6 display recently updated listings and the contents of this category are automatically copied forward from the prior session as soon as a new session is created. This helps provide the best patient care by ensuring the practitioner does not miss any significant risk factors or modifiers.

Figure 7B:
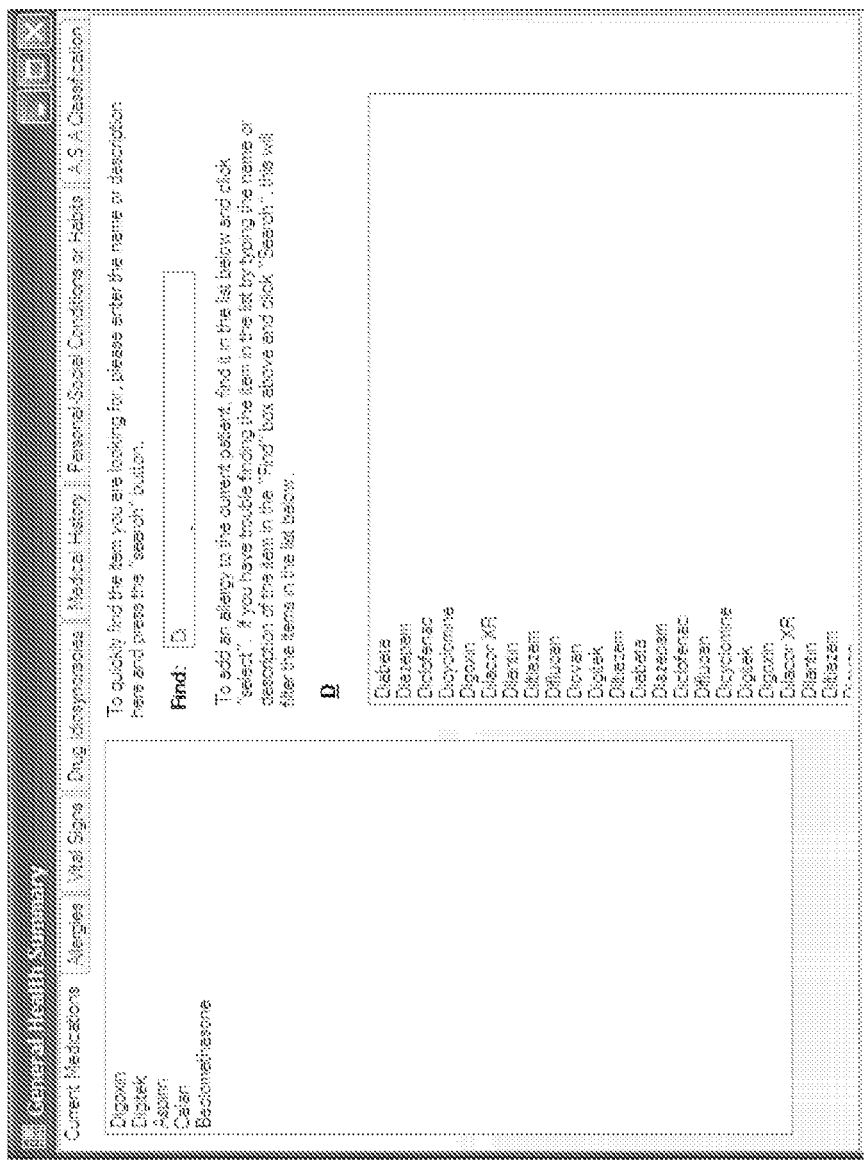

General Health Summary area 7 of FIG. 2 is depicted in particularity in FIGS. 7A and 7B. General Health Summary area 7 of FIG. 7A includes current health status of the patient including terms entered from the glossary (long-term medical conditions which are still of significant concern, allergies, medications, etc.). General Health Summary area 7 displays updated listings and contents that may be automatically copied forward from the prior session as soon as a new session is created. Current medications prescribed by others (medical doctors, etc.) are also shown in General Health Summary area 7. When expanded, as depicted in FIG. 7B, the full General Health Summary is available for review and editing. In this exemplary embodiment, tabs are provided for the following items: Current Medications, Allergies, Vital Signs, Drug Idiosyncrasies, Medical History, Personal-Social Conditions or Habits, A.S.A. Classification.

Figure 8:
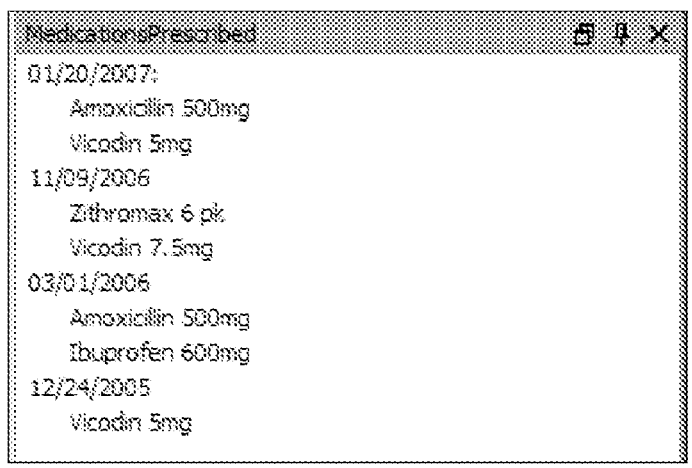
FIG. 8 is a screenshot window pane view of the Prescribed Medications area of FIG. 2

Medications Prescribed area 8 of FIG. 2 is depicted in particularity in FIG. 8. Medications Prescribed area 8, as particularly shown in FIG. 8, lists medications (prescribed and over-the-counter) that may have been prescribed for the patient by anyone in the end-user's practice. Medications Prescribed area 8 includes a listing of prescribed items which are, in the exemplary embodiment, sorted by date. Each item is a summary of an underlying prescription record, which by the practitioner/user activating an item a more detailed record associated with the particular prescription.

Records Management System 102 thus includes a database comprised of a collection of chart entries representing the patient's clinical dental health history record. These records may be organized into rows and columns referencing the totality of the patient clinical dental health history. Chart entries are collected into charts. Each chart may represent a particular aspect of a session between the patient and the practitioner.

Yet another novel aspect of this invention is the concept of a chart view configuration. Chart views define the patient chart content and organization used for viewing or printing. These include specialized reports, letters, presentations, and statistical graphs. Chart views are pre-defined by a knowledge base for immediate use by a practitioner, and are fully configurable for customization if desired. Chart views may be used to define specific data elements of the patient chart (columns), filter for specific data (queries), and organize data into groups, order data (sort), and dynamically format data (fonts/color/style). Any combination of information may be obtained using configurable chart views. Configuring each Patient Chart is optional, and the practitioner or administrator may specify certain default views for general use.

The specific types of chart view configurations are provided, in the exemplary embodiment, as Chart Filter(s), Chart Graph(s) or Chart Report(s). Chart Filters allow the user to quickly find specific chart entries by selecting a term from a listing of categories or sub-categories, and then activating the chart filter (view) mode. This feature adds the ability to filter the patient charts on multiple category terms at the same time as well as applying chart views to better organize the result presentation.

Chart Graphs supports the ability to view patient chart information in many different graphical formats. The user may combine Chart Filters with Chart Graphs to produce trend information on just about anything related to the patient chart records.

Chart Reports are based on similar principles as Chart Filters. Any patient chart information may be sent to a local printer for report generation using all of the same configuration features offered by chart views. A difference between a chart view and a chart report is that grouped terms are organized as blocks and sub-blocks in the report output. Additionally, any application display may be sent to the local printer using the built-in web browser print function.

The view configuration provides dynamic formatting to a particular view (i.e. Chart Filter, Chart Graph, Chart Report). For example a particular view may highlight terms that are more important than other terms such as medical alerts or a particular treatment plan as differentiated from the actual treatment provided. This is called dynamic formatting because each column or data item is evaluated against specific configuration criteria and configuration formatting styles are applied to the data as it is displayed in a current view. The formatting styles include font, coloration, and other types of text and graphics formatting. In this way the practitioner or administrator of this invention can customize how the Patient Chart is displayed according to his/her own preferences. Dynamic value based formatting configurations can be defined for each patient view listing rows or graphics for patient clinical chart history with value based formatting styles.

The view configuration is used to present information according to view configuration rules for (Reports, Graphic Charts, and Letters), and takes the dynamic information returned from the view configuration and inputs into the predefined presentations. In the exemplary embodiment, standard 'views' are defined in the initial setup. The practitioner/user, however, can add new 'views' to sort and view the data from the Patient Chart(s) as s/he finds most useful. Such views may be configured for different viewing devices, so that hand-held devices such as PDA and/or telephones (either cellular, radio, or VoIP) may receive, display, and receive input on such views. Thus, a practitioner's office may be configured to provide such views on multiple types of devices, adapting to the style and parameters of the individuals in the office. Thus, a practitioner might in one circumstance view and edit a patient record in the middle of an examination or procedure using such a hand-held device. In other circumstances, a practitioner may use a full computer and display to examine, make notes, and plan further procedures remotely from the patient.

Another aspect of the present invention relates to a Dental (or Medical) Smart Procedure-Specific Forms Generator. In the exemplary embodiment, this component involves a rules-based dental record entry system in which the current context provides a specific template form associated with a selected category or sub-category. The selected template form is used to fill in data fields relating to the patient and to guide the creation of forms narratives. After starting a new session, a dialog box is displayed with choices of Specialty Type ('Type') and Sub-Category Type ('Sub-Category') and depending on the Sub-category Type selected, it may include another choice: 'Procedures'. 'Procedures' is selected from a dropdown list that would be specific to the selected 'Sub-category.' Appendix A provides a sample of dropdown lists containing dental-specific terms for Types, Sub-Categories and Procedures.

The end-user is able to make multiple selections from Type 'Specialty', Sub-category 'Type' and Procedure lists resulting in a compound template made up of the specific items that had been selected but always in the order of Types, Sub-categories, and then Procedures. The Smart Form Generator filters the entire glossary and displays only those items that pertain to the specific tasks being performed and documented during a particular session. Each general type of form (Examination, Non-surgical care, Surgical care) provides a default set of tabs for individual pages relating to information relevant for the overall form. For example, in the exemplary embodiment the Examination includes at least the following tabs: Chief Complaint, History, Health Summary, Clinical Findings, Radiographic & Lab Findings, Diagnoses, and Treatment Plan. As another example, the exemplary embodiment of the Non-surgical care form includes at least the following tabs: Chief Complaint, POH (personal oral hygiene), Clinical Findings, Radiographic Findings, Treatment (performed), Intra-op Findings, Local Anesthetic, Further Needs. The exemplary embodiment of the Surgical care form includes at least the following tabs: Pre-op (including Indications and Goals of the Procedure), Procedure (description), Intra-op Findings, Suturing & Coverage, Local Anesthetic, Pre-discharge Summary, and Analgesia. The practitioner/user may select from a brief form (standard data entry), comprehensive form (enhanced standard data entry), and a customized form (specific user defined selection of possible data entry). Presenting the specific terms on each page in something similar to a paper-based form only requires mouse clicking on check boxes, selecting a single item from a drop-down list or selecting multiple items from an options list. Unusual comments are typed into a text field.

Figure 15:
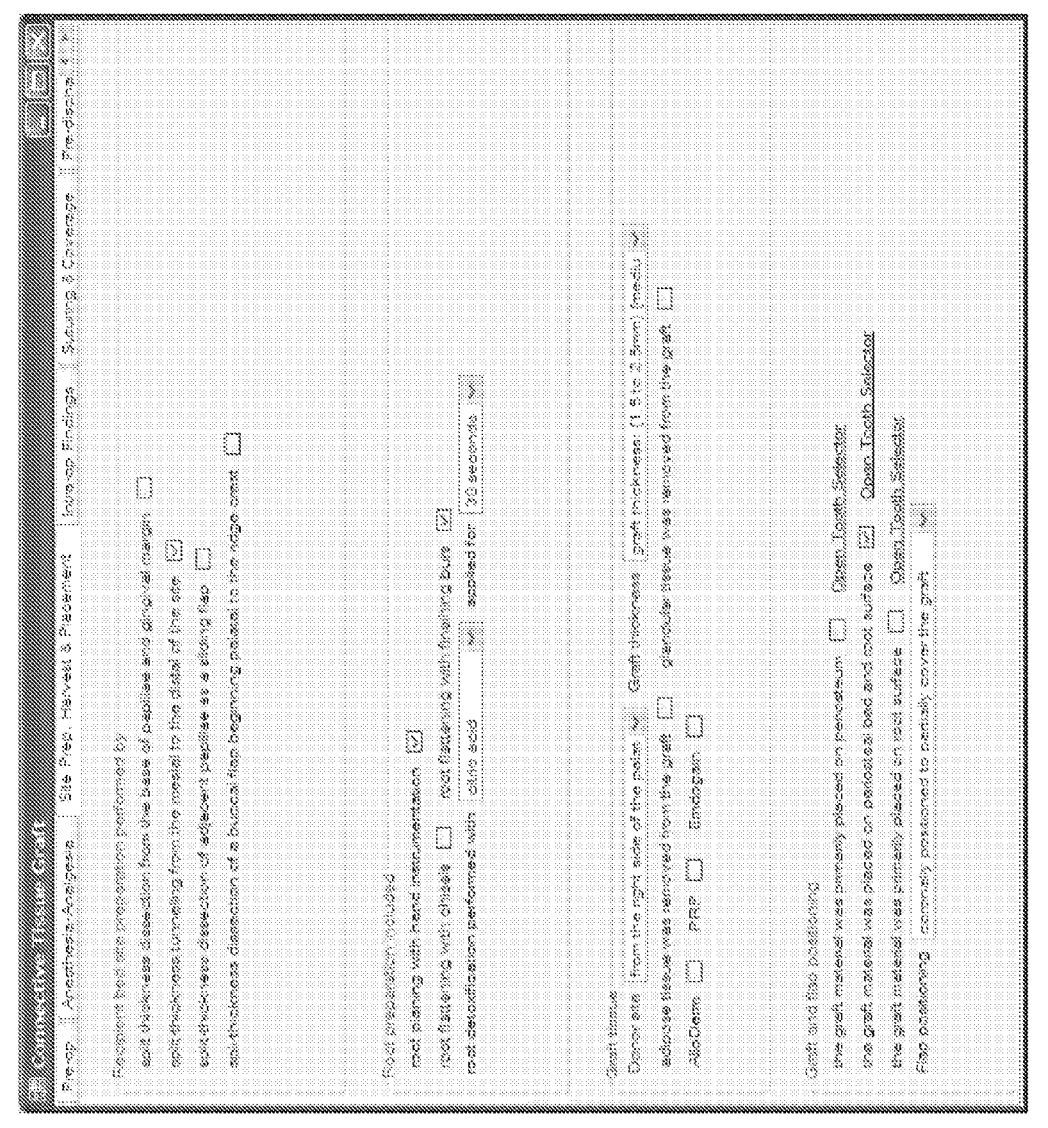

One example present in FIG. 15 and Appendix A involves a scenario in which Surgical care is selected as the category of the form, and-Periodontal is then selected as the Sub-Category. A list of Procedures for the selected Type/Sub-Category is then displayed. For example, 'Connective Tissue Graft' may be selected to lead the user to the template shown in FIG. 15 and Appendix B. In particular, FIG. 15 depicts the particular screen displayed to the practitioner/user when the tab "Site Prep Harvest & Placement" is activated. Template forms are discussed below in relation to a third component of an embodiment of the present invention.

Figure 16:
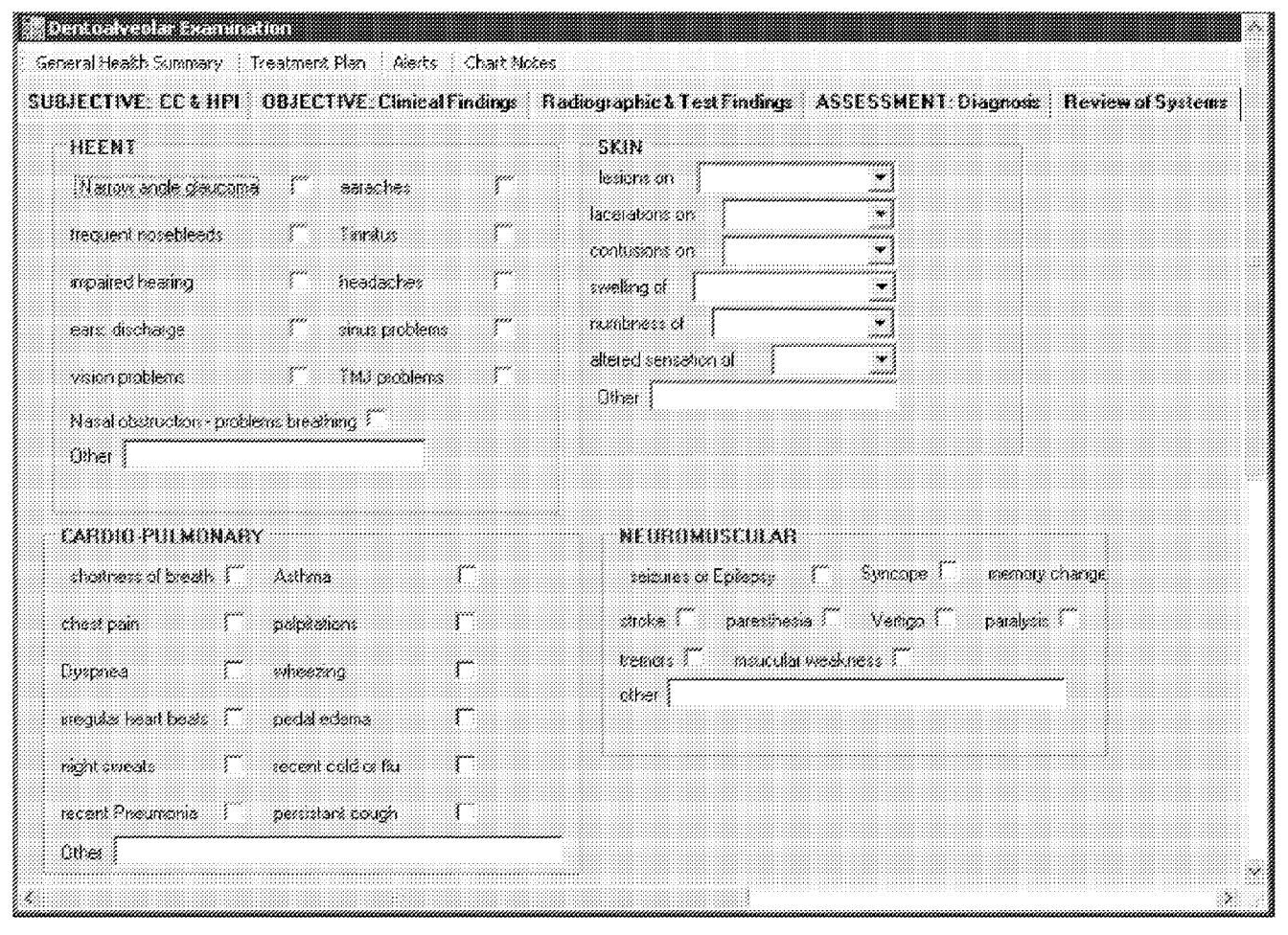

A further aspect of the present invention involves an Input Mechanism for Building Session Content from 'Templates/Forms.' After selecting a Type/Sub-Category/Procedure combination, a particular Template is displayed for the user. 'Templates' are electronic forms that contain multiple data fields specific to a particular procedure or process, typically in a screen having multiple tabs and data entry locations. They give a familiar look and functionality to inputting data. In one embodiment, Templates are pre-existing documents stored in Template Library 108, which when invoked from a current session, inheriting the information from the patient and session. In an alternative embodiment, Templates are created dynamically based on the selected combination, a Template rule, and initial data entries relating to the patient and the session. User selections define input prompts for accepting selectable patient-related data. The user is presented terms in a template or electronic form from which he/she will (1) click on check boxes, (2) make single selections from dropdown list boxes, (3) make multiple selections from multiple options boxes or (4) write in blank text fields. FIG. 16 shows an exemplary input screen for a procedure, in this case a Dentoalveolar Examination. Each form may have several tabs each with several data entry fields. When the user finishes making selections from the template, he/she clicks a button (Save) which re-compiles the selected items along with their appropriate parent terms to display in prose format or bulleted format. Some or all of the tabs of a particular form may be completed. The display may create documents that are editable (e.g., using a word processor) to allow the addition of comments or further details at any location within the document, or may create an image file suitable for direct printing. Appendix C shows a sample of prose-formatted output in such a document. Appendix D shows a sample of output in bulleted format.

Figure 11:
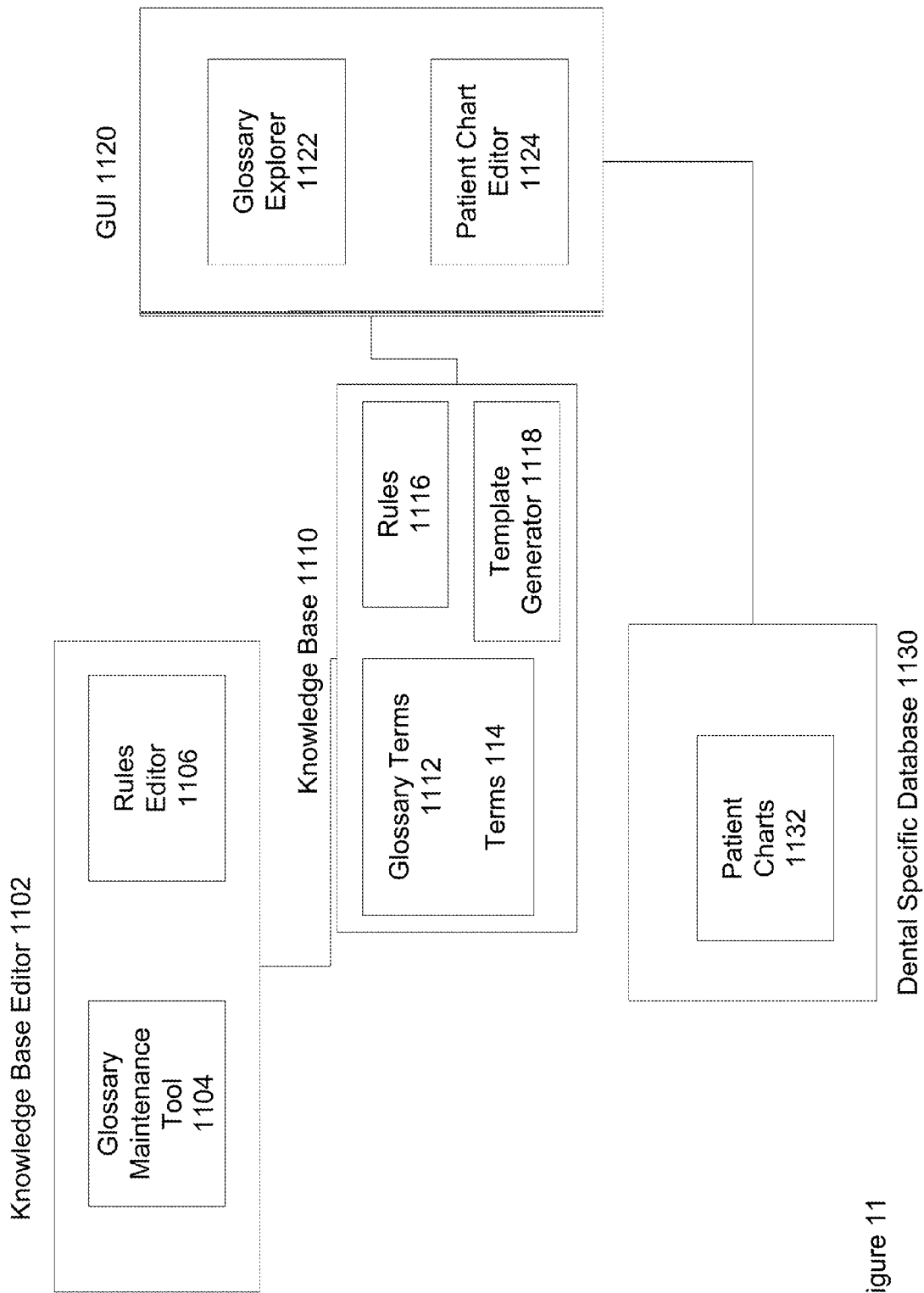
FIG. 11 is a schematic diagram of the knowledge base feature in one embodiment of the present invention.
Figure 12A:
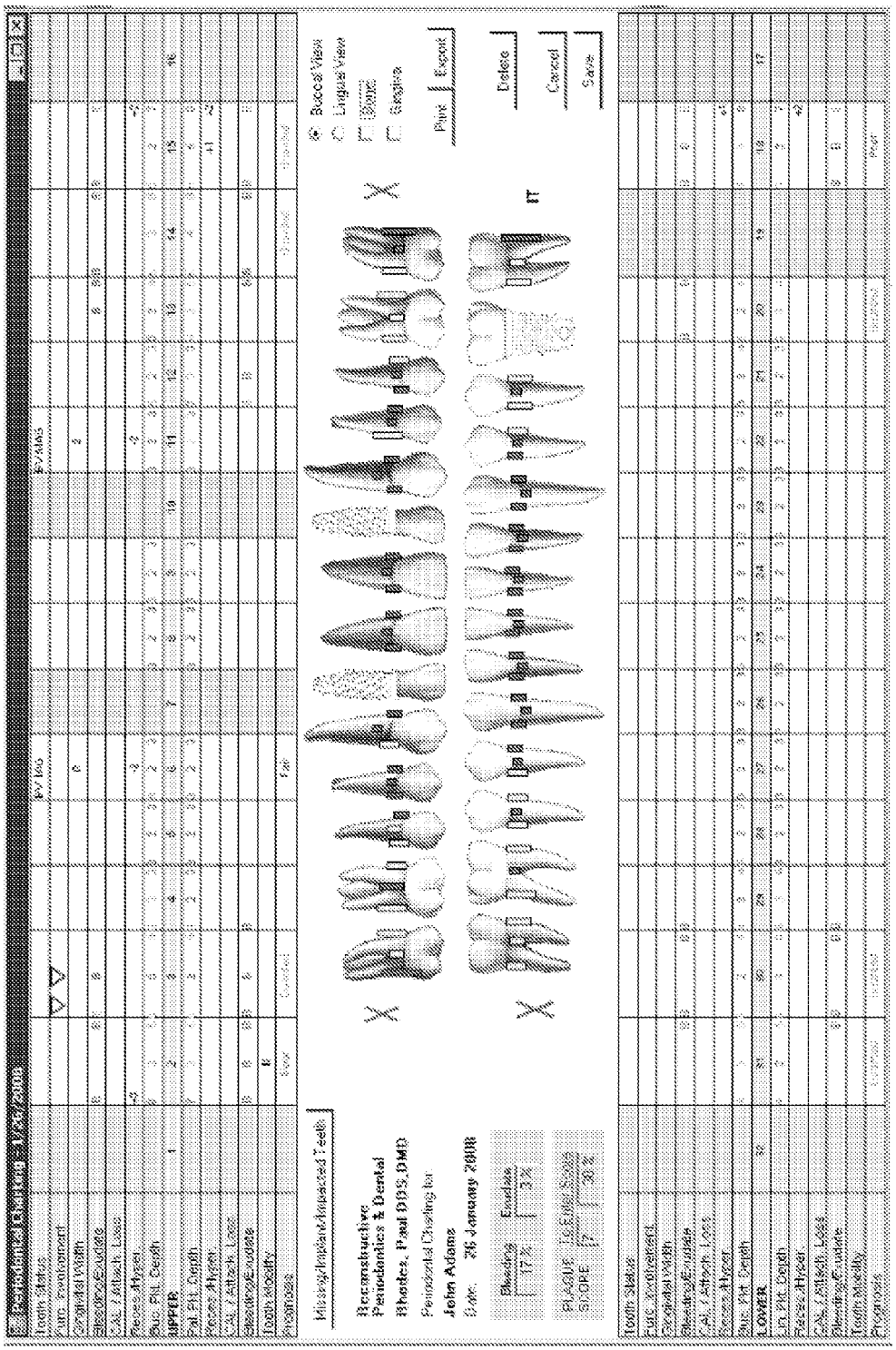
FIGS. 12A-12D are screenshot views of a periodontal charting spreadsheet screen relating to the Dental Chart of FIG. 4.
Figure 12B:
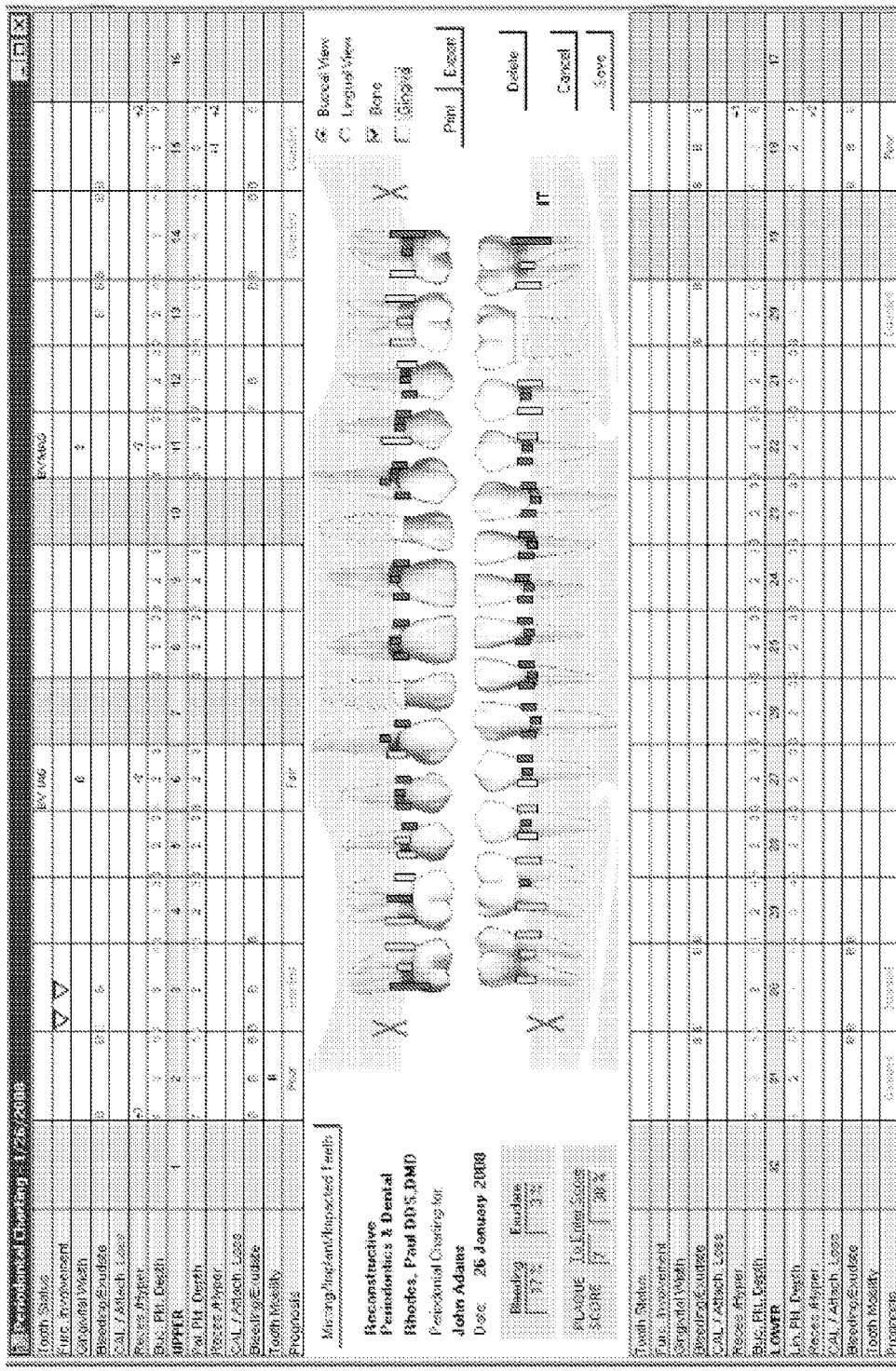
Figure 12C:
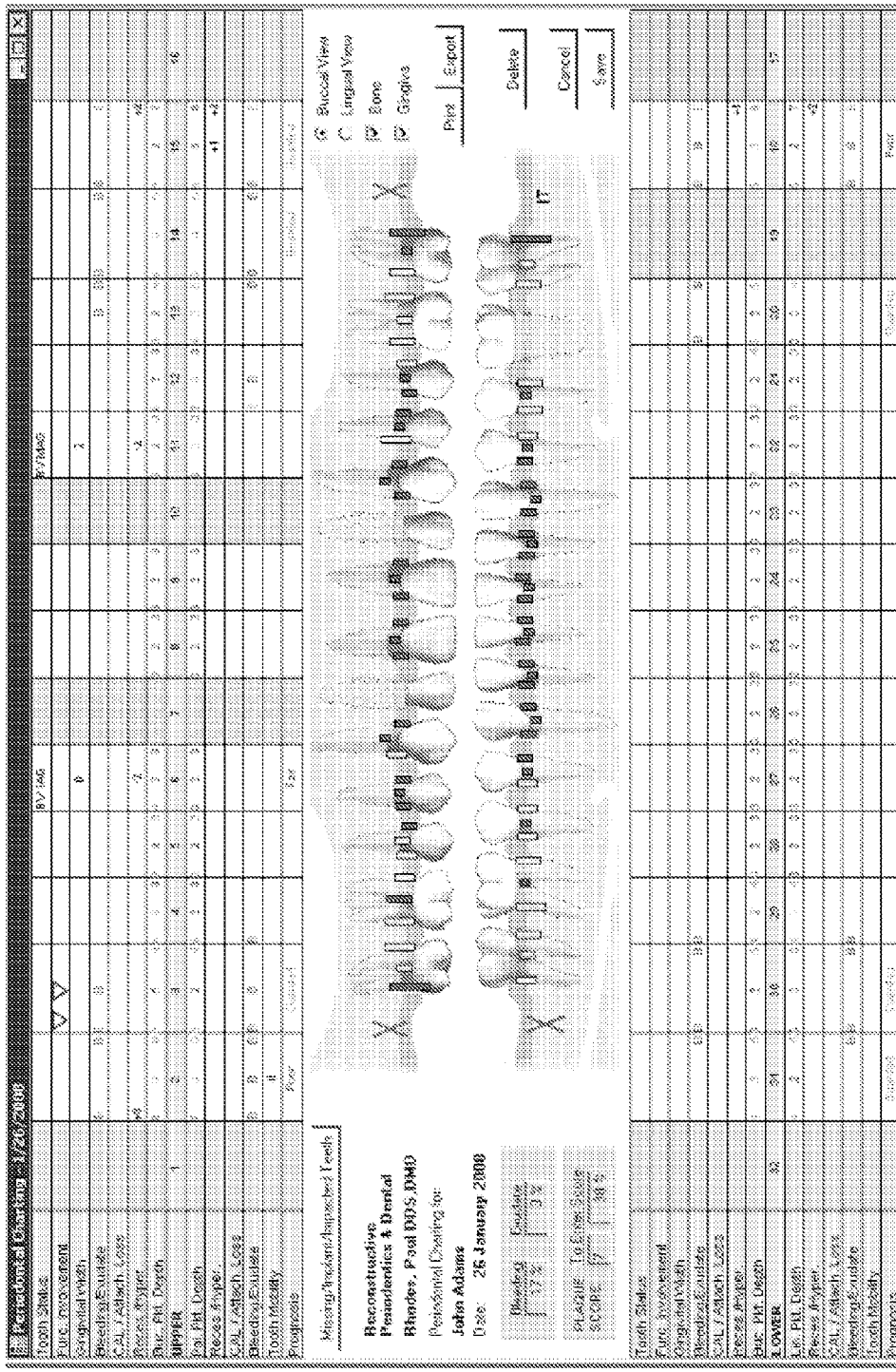
Figure 12D:
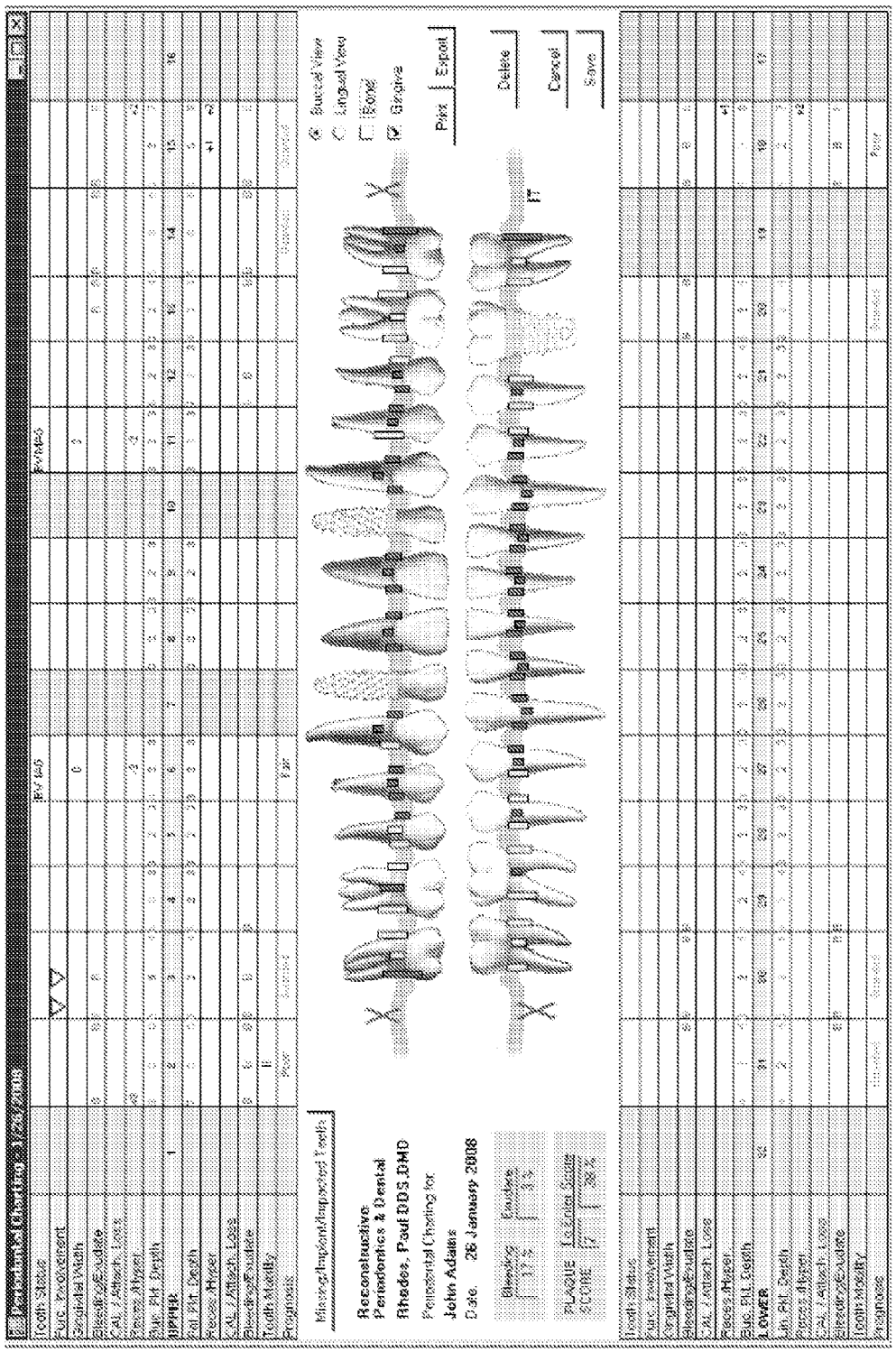

Clinical records management system 102 is based on Knowledge Base 108 (FIG. 1). FIG. 11 depicts further details of the Knowledge Base feature. Main GUI 1120 effectuates an efficient and smooth flow of data entry by utilizing Knowledge Base 1102. Knowledge Base 1102 houses terminology common to several dental specialties and rules to guide the creation of Templates and Forms. In building session content, the user selects a specific Type/Sub-Category/Procedure combination matching the procedure being administered to patient. Template Generator 1118 dynamically creates a template/form using the user-selected combination, Glossary Library 1212 and Rules 1214. Rules 1114 define how Glossary Library 1112 is organized, associations between terms and procedures, and how Procedure-specific Forms and Templates are generated and displayed. Each Form has various tabs that display specific areas of information related to the specific procedure selected and covered in the form. Glossary Library 1112 and Rules 1114 may be updated by an administrator via a software update or 'patch' (either locally or remotely) or manually using Knowledge Base editor 1102. Knowledge Base editor 1102 may be used by a practitioner/user to hide certain data elements in particular forms, either in the data entry or the report/letter generation. Another aspect of Knowledge Base 1102 involves the translation of entered data into either text suitable for a letter or a bullet point report. For example, the bullet point report of FIG. 17 includes textual information relating to several forms, from patient general data, to a session examination, treatment, and anesthesia.

Main UI 104 also includes access points for Glossary Explorer 1122 and Patient Chart Editor 1124 of FIG. 11. In addition, and as part of the user interface, there is a method of creating and editing the Glossary Library 1112 called Glossary Management Tool 1104, configuring user interface layouts, and predefining various organizational aspects of the Glossary Library 1112 by the administrator of knowledge based clinical records management system 102. Rule Editor 1106 is used to update rules governing the relationship between procedures and terms, including the form and content of procedure forms and documents. Glossary Management Tool 1104 and Ruled Editor 1106 are components of Knowledge Base Editor 106 (FIG. 1). Glossary Library 112 also includes information on specific types of data so that multiple levels of detail may be easily navigated by the practitioner/user. For example, in the exemplary embodiment, certain types of dental materials may be specified in a cascading fashion so that once a practitioner/user selects a particular company, the various styles available from the company are displayed for selection, then the applicable diameters for the style are displayed for selection. Similarly, when entering a suture material, a practitioner/user may first specify the actual material being used in the procedure and a drop-down menu of related diameters is then displayed.

In addition to selecting items from pull-down menus, the typing feature matches the initial few letters entered by the user with the glossary terms relevant to that portion of the patient record. Thus, if the user attempts to type in a glossary term that is inappropriate to the current entry information of the record, no match would be found. This allows a practitioner/user to enter information that is not in the predefined glossary if appropriate, and also provides a tool to check the spelling and appropriate use of a free text term. A further embodiment of the invention also provides a pop-up window with a message that explains why the typing is inappropriate to the current entry and/or suggests alternatives that the knowledge engine determines may be the intention of the user.

The right clicking function allows the user the ability to filter the patient's records and present only those sessions containing information on the user-selected category or term and within each such session only the information included in the selected topic. Glossary filters allow users to limit the glossary content to a specific category or terms that contain a specific phrase. This reduces the time spent browsing the glossary for specific terms, and reduces the time a dentist would need to spend finding a data record relevant to the glossary term selected.

Figure 9A:
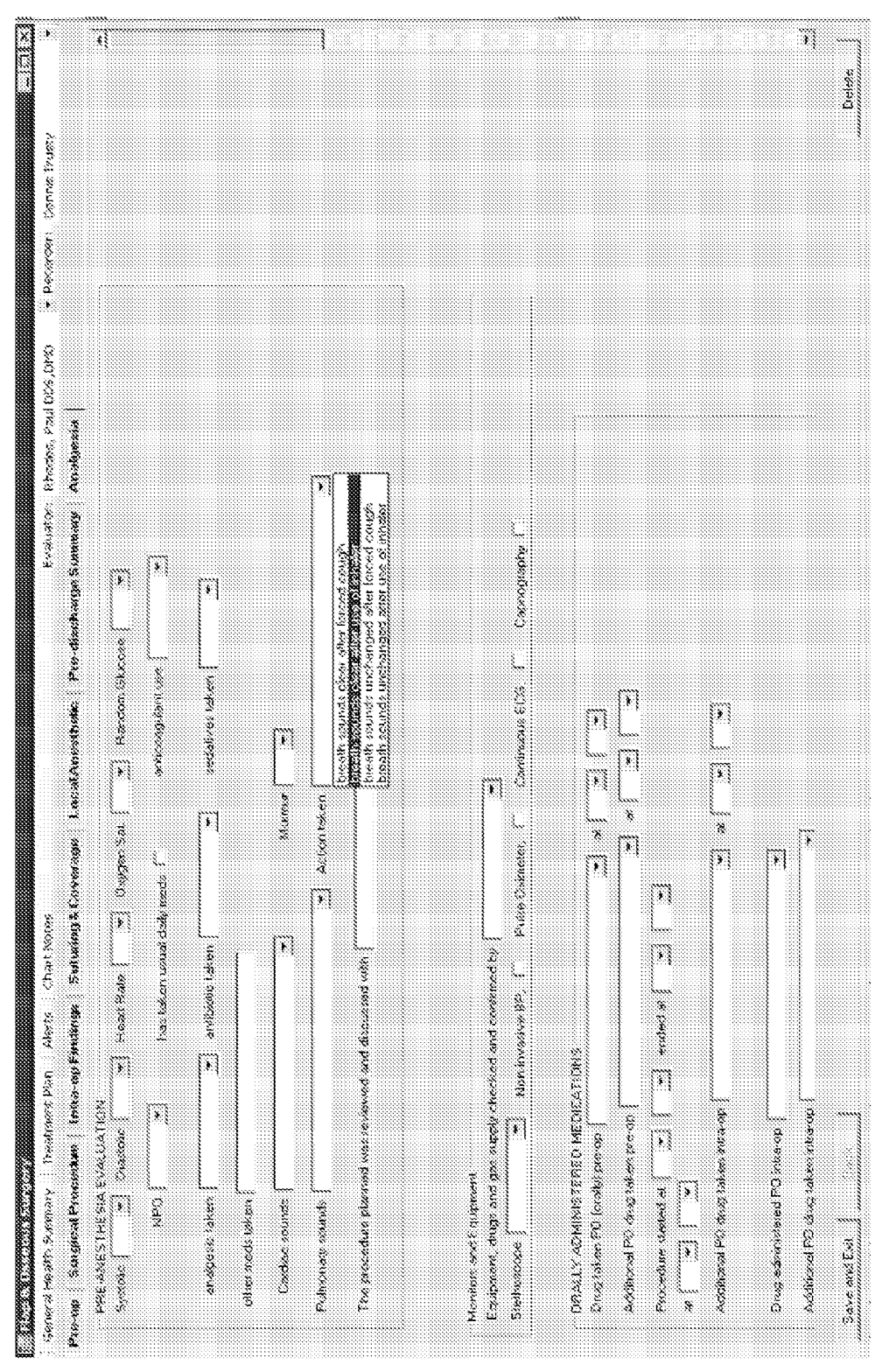
Figure 9B:
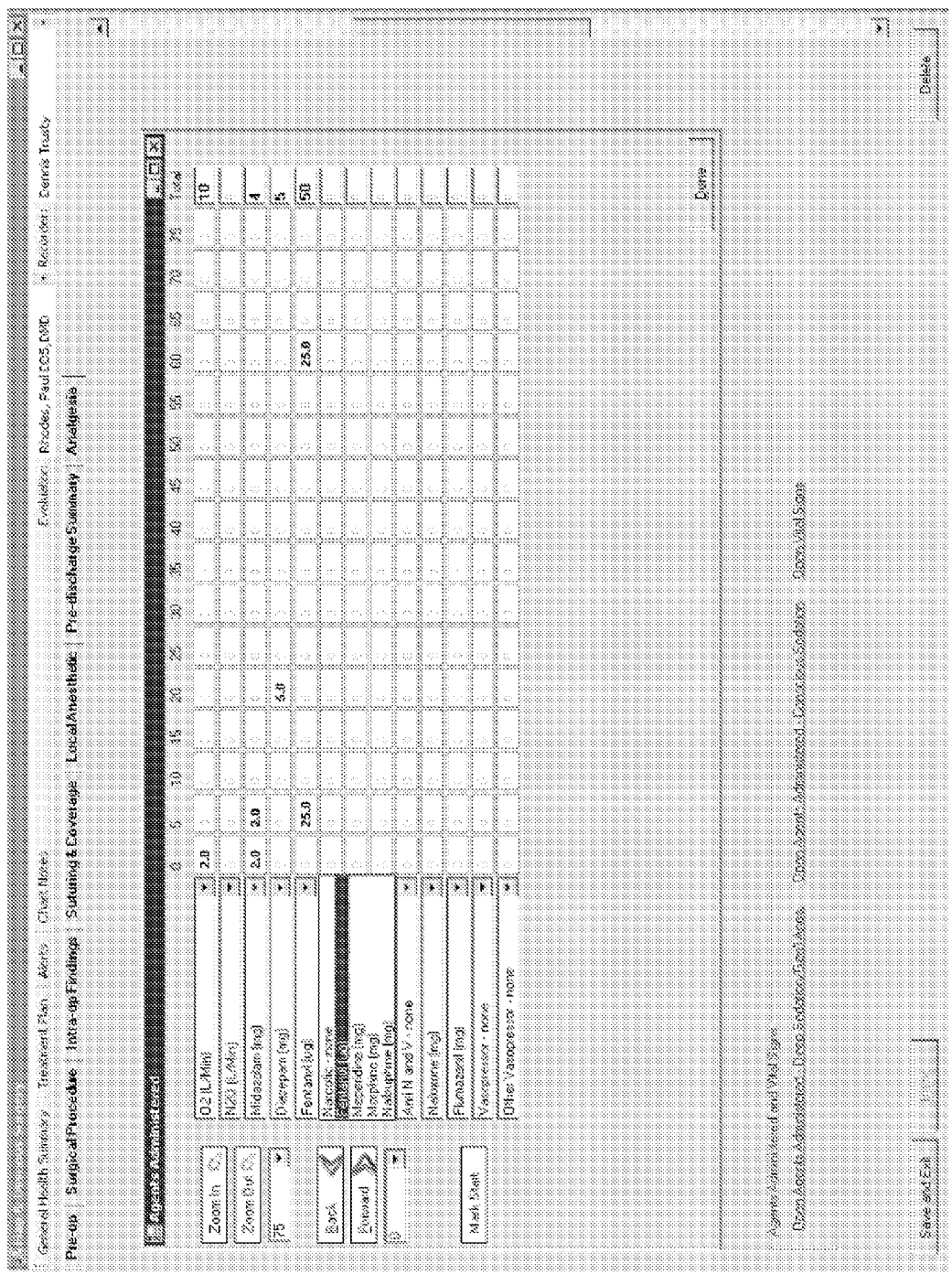
Figure 9C:
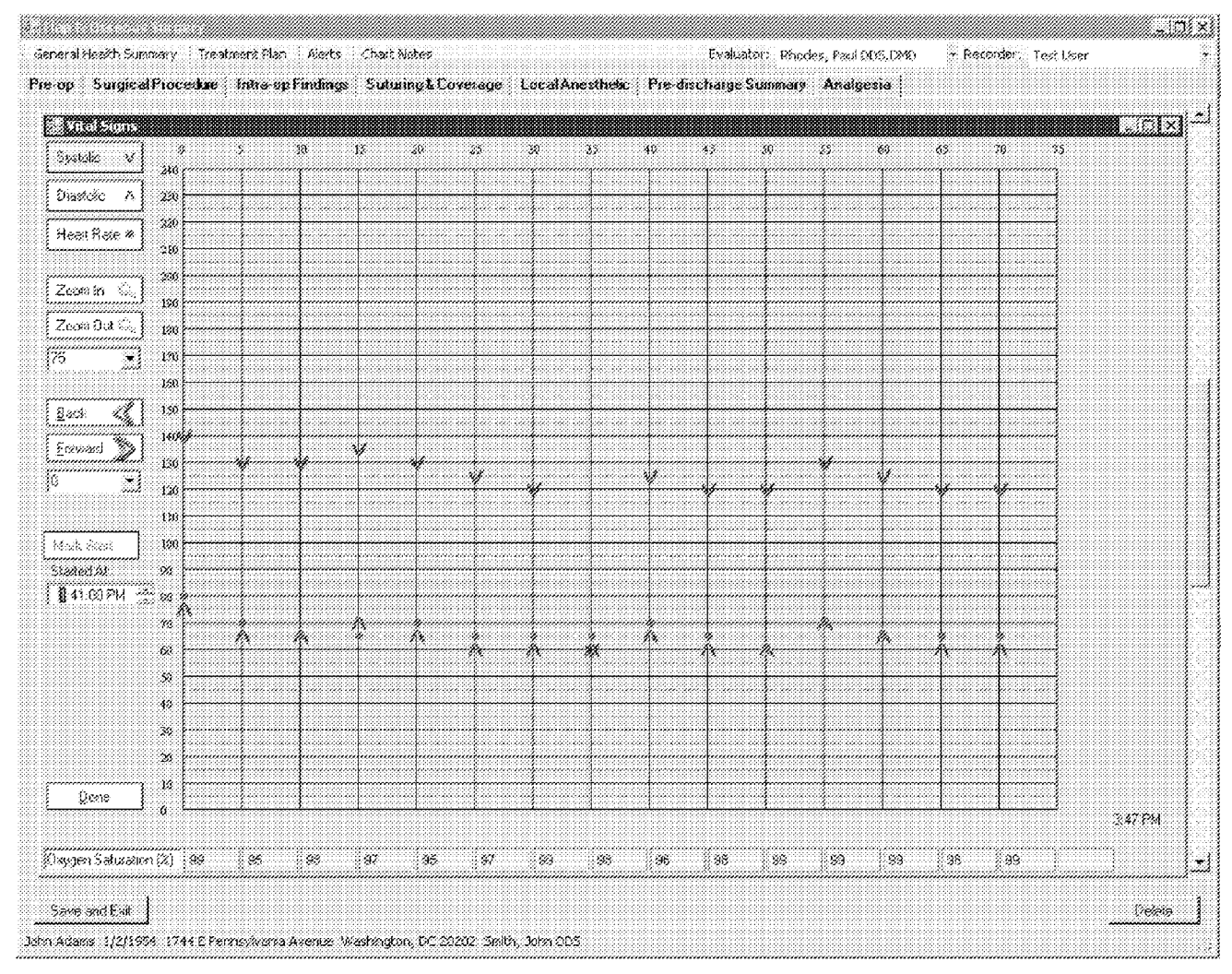
Figure 9D:
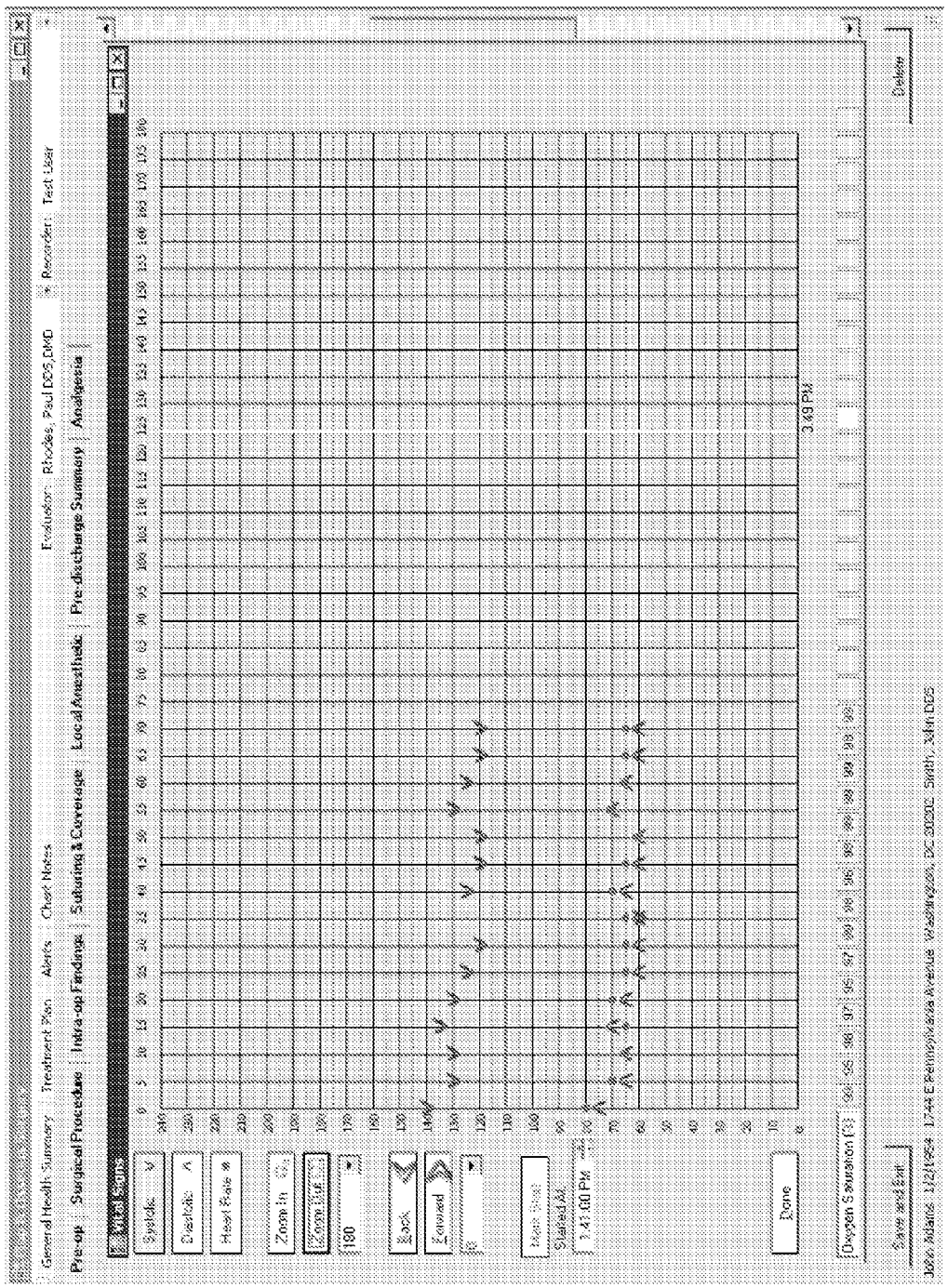
Figure 9E:
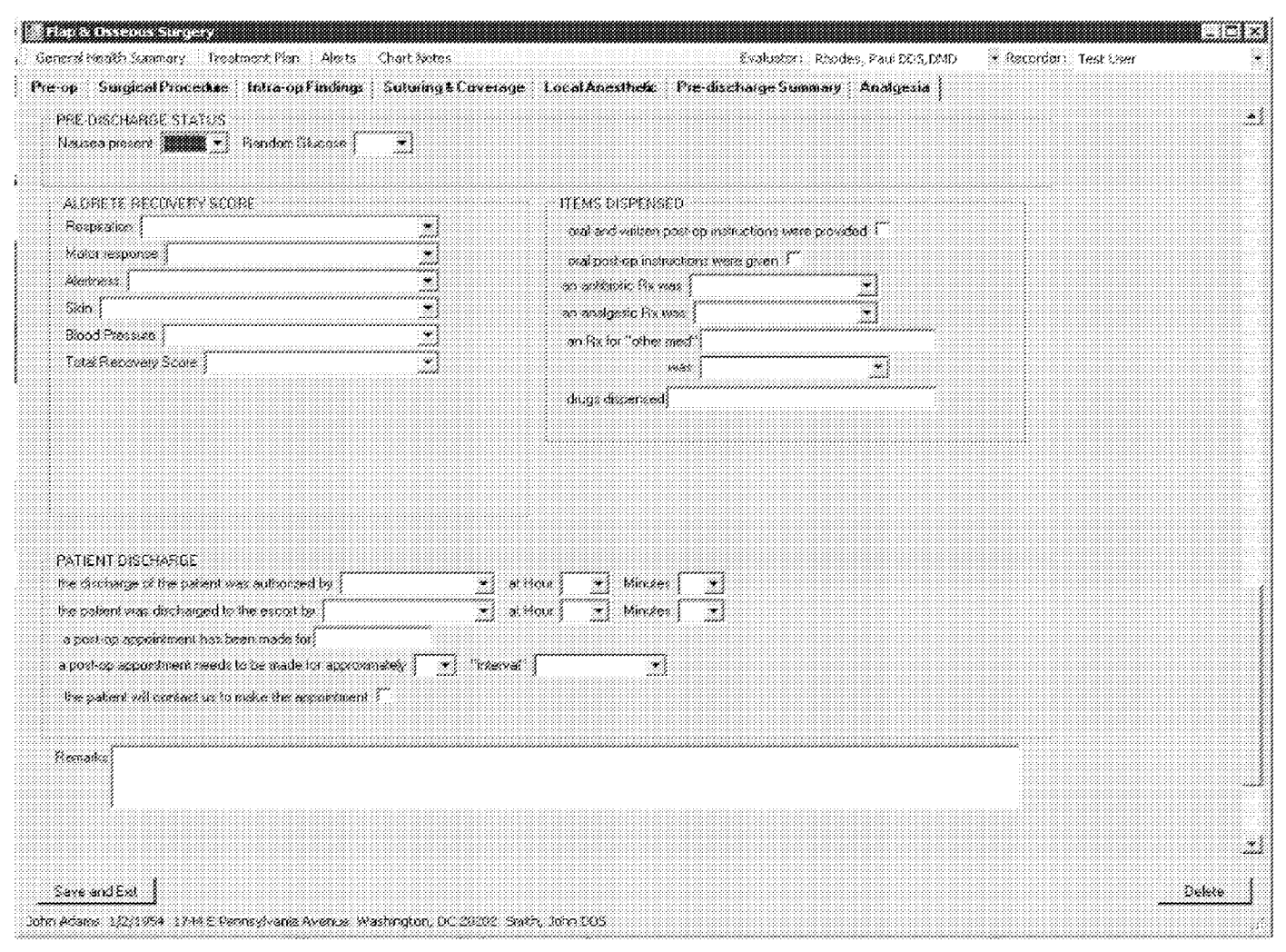
Figure 10:
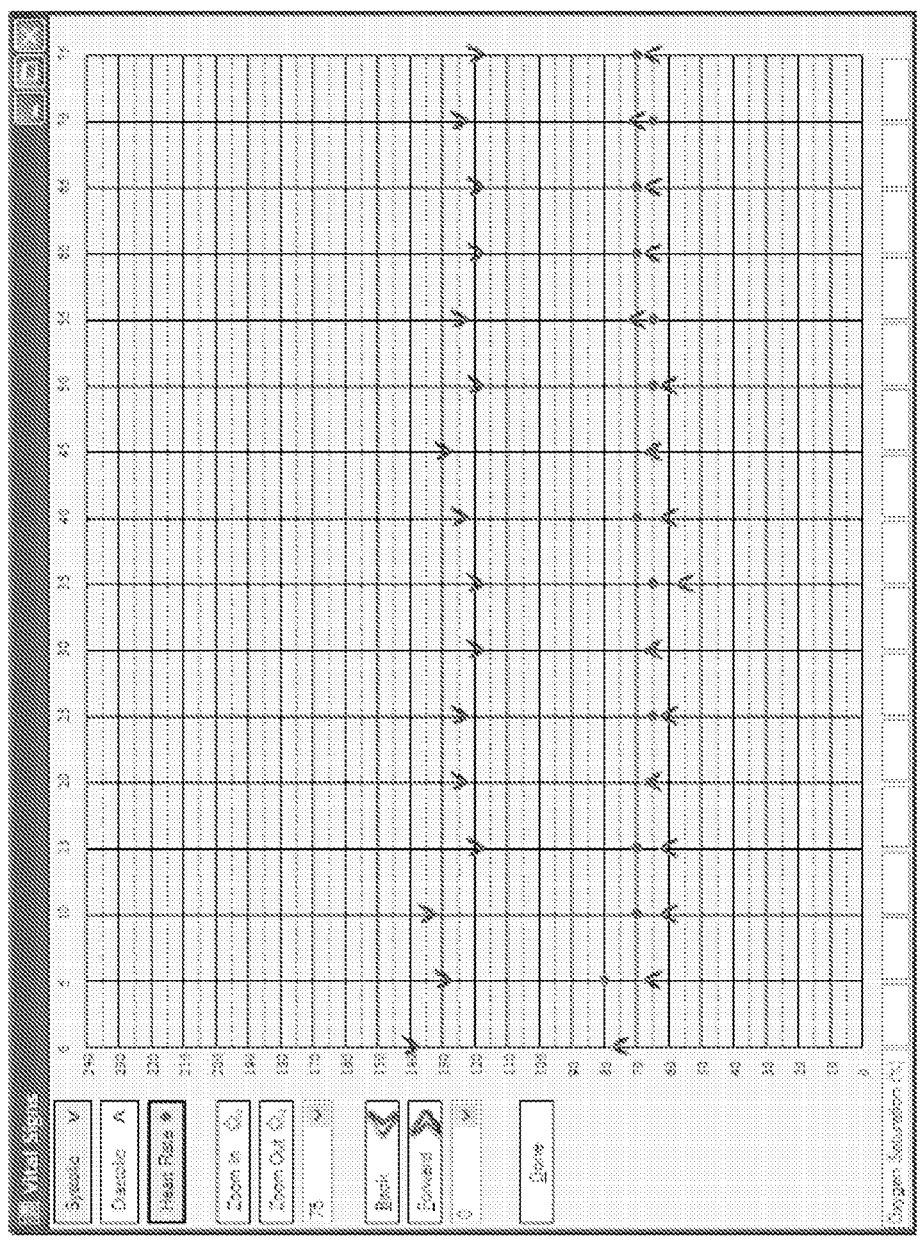
FIG. 10 is a screenshot view of the Vital Signs page relating to the Anesthesia Record page of FIG. 9.

An additional aspect of the present invention relates to the Anesthesia Record depicted in FIG. 9. Anesthesia Record data is stored in Database 114. Each Anesthesia Record contains data related to the administration of an anesthetic modality, for example such modalities such as: local anesthesia, orally administered conscious sedation, I.V. administered conscious or deep sedation, I.V. Administered general anesthesia or Inhalation General Anesthesia. Each Anesthesia Record is broken down into several sections, with this exemplary embodiment including: (1) Pre-Anesthesia Evaluation, (2) Monitors and Equipment, (3) Orally Administered Drugs, (4) Anesthetic Technique, (5) Airway Management, (6) I.V. Antibiotics Administered, (7) Anesthetic Agents Administered, (8) Vital Signs and (9) Pre-Discharge Evaluation and Status. An exemplary embodiment of a Vital Signs page, in one form, is depicted in FIG. 10. The Vital Signs page provides information from a device monitoring at least one of the patient's blood pressure, heart rate and blood oxygen saturation during a dental procedure, with the example of FIG. 10 showing the tracking of blood pressure heart rate and oxygen saturation. However, other vital signs may be monitored and included in a Vital Signs page. Multiple Vital Sign pages may be associated with a anesthesia record, for example, a patient may have heart rate, blood pressure, temperature, and galvanic skin response measured during an anesthesia event and recorded on separate Vital Signs pages. The anesthesia record may be adjusted to the time duration of the procedure, showing all data on one page or zooming in a specific time block to show data in greater size for ease of accurate viewing. Also back and forward buttons allow for the view to move forward or reverse to view different time blocks of data.

The layout of the Anesthesia Record page is determined based on the anesthesia type. Different types will hide different categories and sub-categories. Thus, each Anesthesia Record includes information about dosages of anesthesia delivered to the patient and data related to the patient's response to the anesthesia. Having a distinct Anesthesia Record allows for disparate medical and/or dental practices to share information about a specific patient's reaction to anesthesia. An exemplary collection of Anesthesia Record screen shots are provided in FIGS. 9A-9E illustrating various aspects of the Anesthesia Record. FIG. 9A represents a pre-examination record with the ability to record the patient statistics prior to dispensing anesthesia. FIG. 9B illustrates the charting ability to include specific medications and dosages at various times administered during a procedure. FIG. 9C illustrates a monitored vital sign such as blood pressure being monitored across the time domain. FIG. 9D illustrates a similar view as FIG. 9C except with the temporal domain being graphically compressed. FIG. 9E illustrates a discharge record relating to the anesthesia event.

The variations of the Anesthesia Record may be dynamically created once the modality is specified. For example, a record of Local Anesthesia may include sections (1) and (2); section (3) excluding anything dealing with General Anesthesia or Conscious Sedation; section (4) including only Nasal Mask and Nasal Cannula choices; omitting sections (5) and (6), including section (7) and section (8) except omitting the Aldrete Recovery Score and adding the notations 'Patient discharged to escort . . . .' As another example, an Anesthesia Record relating to Orally Administered Conscious Sedation may include sections (1) and (2); section (3) and section (9), excluding anything dealing with General Anesthesia or I.V. Conscious Sedation, but include a list of orally administered analgesic agents including the times they are administered; section (4) including only Nasal Mask and Nasal Cannula choices; omitting section (5) and (6), and including sections (7) and (8). With the example of I.V. Administered Conscious Sedation, such an Anesthesia Record may include sections (1) (2) (4) (5) (6) (7) (8) and (9); section (3) excluding anything dealing with General Anesthesia; section (4) including only Nasal Mask and Nasal Cannula choices; omitting section (5) and including sections (6), (7) and (8). With an Anesthesia Record relating to I.V. Administered Deep Sedation/I.V. or Inhalation General Anesthesia all sections are included.

Figure 13A:
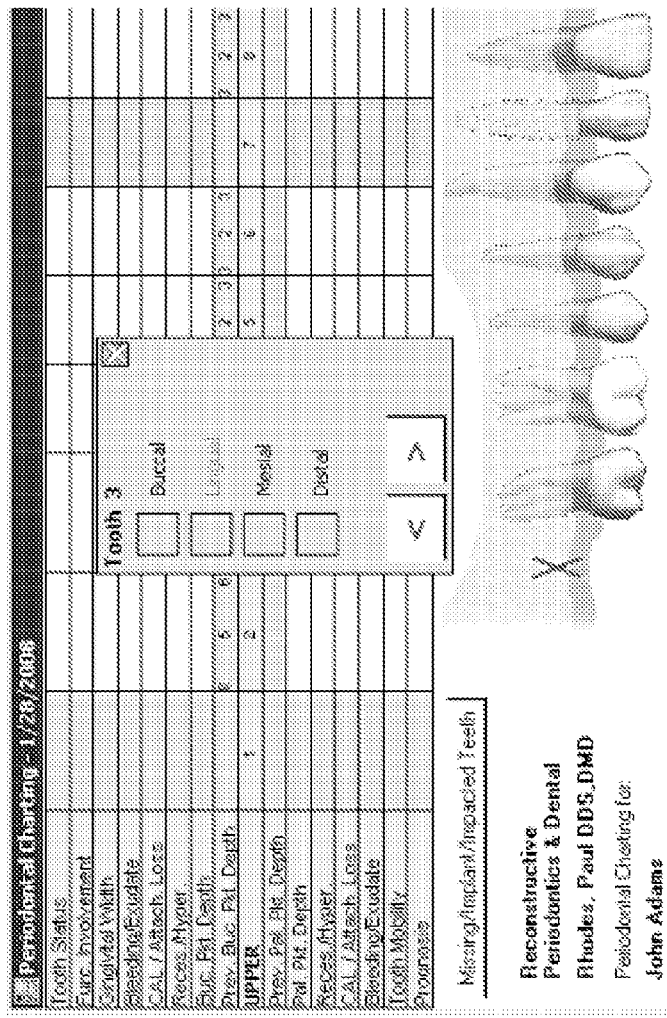
Figure 13B:
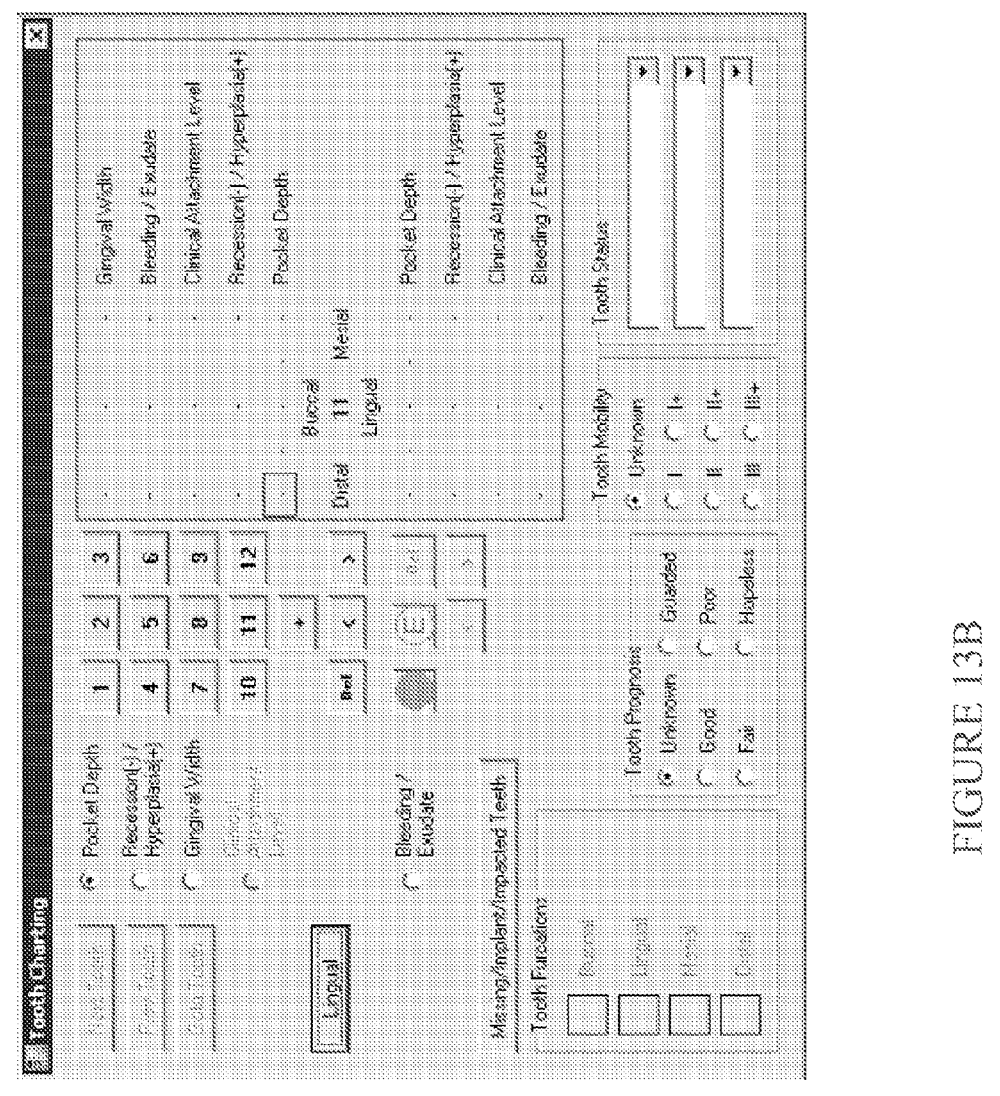

Another aspect of the present invention relates to a unique set of data and display (UI) known as the 'PerioProfile.' Periodontal charting involves the collection of multiple parameters of site specific information. It can be done either one tooth at a time or more commonly it is done one parameter at a time by making a circuit through the mouth for each parameter. The PerioProfile allows for three different ways of entering data: (1) a circuit approach which follows the user defined path through the dentition to put in a single data parameter for all teeth at a time; (2) enter a single parameter on a single tooth; or (3) enter all parameters of data at once on a single tooth. FIG. 13A depicts how the user would enter a single data parameter on a single site—while FIG. 13B depicts a periodontal charting input for all data parameters for one tooth. The parameters entered on the screens of FIGS. 13A and 13B result in the Perio chart format shown in FIGS. 12A-12D. In addition to the data values collected and included on a traditional periodontal chart, the PerioProfile may collect and simultaneously display data on signs of inflammatory activity and produce indices for 'Bleeding' and 'Exudate' activity; collect and display data on a patient's plaque control effectiveness (a 'Plaque Score'), and other strategic items of dental and periodontal morphological data pertinent to periodontal evaluation such as including the display of normal supporting bone and extent of gingival tissue overlaying the graphical periodontal data display to allow the viewing of the relationships between anatomic structures and the extent of periodontal destruction also shown in FIGS. 12A-12D.

Traditionally, the display of periodontal charting has been arranged around a graphic of the teeth and has utilized numbers as well as universally recognized symbols (for example, Roman numerals for tooth modalities). In one embodiment of the present invention, the display of periodontal charting is done by displaying alphanumeric data in a 'spreadsheet' format so that data for a specific site can be readily reviewed by scanning down a vertical column. FIGS. 12A-12D depict periodontal charting spreadsheet screens. Additionally, this same data is display graphically around graphics of individual teeth and implants and may include an overlay of periodontal supporting bone (FIG. 12B) and/or gingiva (FIG. 12D, both supporting bone and gingiva in FIG. 12C) to show the relationship between data items and these anatomic structures. This comprehensive spreadsheet and graphical view of periodontal data is a unique design feature of this application.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains. The following Appendices provide examples of aspects of the present invention, which may be altered and adapted in various forms.

Appendix A shows a List of Type-Sub-Category-Procedure combinations for development of procedure-specific templates used in the present invention.

Appendix B shows a sample template used in the present invention.

Appendix C shows sample output of the present invention presented in prose format.

Appendix D shows sample output of the present invention presented in bulleted format.

APPENDIX A

List of Type-Sub-Category-Procedure
combinations for development of 94 procedure-specific templates Examination, Consultation, Reevaluation (8)

Periodontal including Mucogingival
Reconstructive (tooth related)
Dentoalveolar/Regenerative
Implant
Orthodontic related
Oral Pathology
Esthetic/Plastic
Parafunction/TMD
Consultation (for the presentation of a treatment plan) (8)

Periodontal including Mucogingival
Reconstructive (tooth related)
Dentoalveolar/Regenerative
Implant
Orthodontic related
Oral Pathology
Esthetic/Plastic
Parafunction/TMD
Reevaluation (after further diagnostic aid or initial therapy) (8)

Periodontal including Mucogingival
Reconstructive (tooth related)
Dentoalveolar/Regenerative
Implant
Orthodontic related
Oral Pathology
Esthetic/Plastic
Parafunction/TMD
Non-surgical treatment (1)

Non-surgical treatment
Oral Hygiene Instruction
Periodontal Maintenance Care
Adjunctive treatment (5)

Occlusal Adjustment
Fabrication of an Orthotic or Occlusal Inhibiting Appliance
Delivery of an Orthotic or Occlusal Inhibiting Appliance
Intra-coronal Splinting of Teeth
Extra-coronal Splinting of Teeth
Implant Abutments, Impressions, Temporaries
Surgical treatment
Gingival (including excisional & flap sx) (7)
Mucogingival Periodontal Flap and Osseous Surgery
Connective Tissue Graft
Flap Surgery
Gingival Graft, Frenectomy, Vestibular Extension
Gingivectomy-Gingivoplasty
Laterally Sliding Pedicle Flap
Flap & Osseous (including flap curettage, ostectomy/osteoplasty and bone grafting/GTR)
Reconstructive (tooth related) (3)

Crown Lengthening
Root amputation/Hemisection

APPENDIX A-continued

List of Type-Sub-Category-Procedure
combinations for development of 94 procedure-specific templates Access & Restore/Repair a subgingival root defect/caries
Dentoalveolar/Regenerative (12)

Simple Extraction of Teeth or Roots
Surgical Removal of Erupted Teeth or Retained Roots
Alveolectomy/plasty
Mandibular lingual tori removal
Palatal midline tori removal
Socket Augmentation
Simultaneous Extraction and Socket Augmentation
Osseous Edentulous Ridge Augmentation
Soft Tissue Edentulous Ridge Augmentation
Maxillary Sinus Lift via Crestal Approach
Maxillary Sinus Augmentation
Screw Removal from Block Graft
Implant (8)

Implant placement in the Edentulous Area
Extraction and Simultaneous Implant Placement
Implant Exposure
Implant Repair/Regeneration
Simple Implant Removal
Surgical Implant Removal and Site Augmentation
Implant Abutment Attachment
Implant Impressions and Temporization
Orthodontic related (2)

Surgical Exposure of Impacted or Unerupted Teeth
Circumferential Fiberotomy
Oral Pathology (2)

Soft Tissue Biopsy
Hard Tissue Biopsy
Esthetic/Plastic (2)

Connective Tissue Graft*
Crown Lengthening*
Post-op care (8)

Periodontal including Mucogingival
Reconstructive (tooth related)
Dentoalveolar/Regenerative
Implant
Orthodontic related
Oral Pathology
Esthetic/Plastic
Parafunction/TMD
Outcomes Evaluation & Summary (8)

Periodontal including Mucogingival
Reconstructive (tooth related)
Dentoalveolar/Regenerative
Implant
Orthodontic related
Oral Pathology
Esthetic/Plastic
Parafunction/TMD
Recurrent Maintenance (2)

Periodontal Maintenance Care
Prostho Appliance Care
Periodic Monitoring-Evaluation (4)

Periodontal
Implant
Pathology
Parafunction/TMD

APPENDIX A-continued

List of Type-Sub-Category-Procedure
combinations for development of 94 procedure-specific templates For example, if the Type was Surgical treatment and the
Sub-catergory was Mucogingival, the list of Procedures
would include:

Connective Tissue Graft
Gingival graft
Frenectomy
Laterally Sliding Pedicle Flap
Vestibuloplasty
Semilunar Coronally Repositioned Flap
Double Papillae Graft Each one of these would have a specific template i.e. the Connective Tissue Graft template of Appendix B APPENDIX A-continued List of Type-Sub-Category-Procedure
combinations for development of 94 procedure-specific templates

APPENDIX B

Surgical Procedure: CONNECTIVE TISSUE GRAFT
Site: # (ToothSite selector)
Purpose: ☒increase CT attachment to root  ☒reduce area of exposed root surface
Recipient Bed Preparation:
Split-thickness sharp dissection
    ☐performed by mesio-distal tunneling
    ☒from the base of the papillae   ☐from the gingival & papillary margins
    ☐including muscle/frenum release at base of incision
Root Preparation
    Instrumentation included
        ☒root planing performed to ☒remove necrotic cementum
        ☒flattening of the root surface
        ☒using curettes   ☐using finishing burs  ☒using hoes/chisels
    Detoxification included:
    ☒Citric Acid applied for 1 minute
    ☐Tetracycline emulsion applied for .....
    ☐Phosphoric Acid applied for .....
    ☐EDTA applied for .....
Graft Source:
    Harvested from the right(side) of the palate  ☐ an allograft material was used
    Thickness:  ☐ thin (<1.5mm)  ☒ medium (1.5-3mm)  ☐ thick >3mm
    Length: 2cm  Width: 5mm    ☐The graft was split lengthwise into two pieces
    Harvest site flap was sutured with  5-0 (size) Monofilament (type)
    Harvest site was covered with   ...... (material) .......(appliance)
Graft Placement
    ☐Graft placed over periosteal bed only  (site selector)
    ☒Graft placed over periosteal bed and root surface  (site selector)
    ☐Graft placed over root surface only  (site selector)
    ☒Anchor sutures were placed at apical border of graft  6-0 (size) Braided Vicryl (type)
Flap Management
    ☐Flap partially covered the graft – part of graft was exposed
    ☒Flap was advanced to entirely cover the graft
    ☐The flap and graft were then sutured using 5-0 (size) - Braided Vicryl(type)
        with interrupted (suturing – multiple choice) suturing
    ☐The graft and flap were covered with ..... (material / appliance)
Intra-operative Findings:
    ☐graft tissue was dense with a smooth under-surface
    ☒graft tissue contained glandular & adipose tissue with an irregular under-surface
    ☒Glandular & adipose tissue were removed prior to placing the graft
Post-operative Status::
    Bleeding was under control
    Patient is comfortable – no significant pain
    Post op instructions were  ☒discussed ☒dispensed
    Rx for analgesic was .....
    Rx for antibiotic was .....

[SAVE]

APPENDIX C

May 21, 2007: Mucogingival Surgery (session title)
CONNECTIVE TISSUE GRAFT #4-5-6 area
  Purpose of this procedure: To increase connective tissue attachment to the root surface and to reduce the extent of root exposure that has resulted from mucogingival recession.
  Recipient Bed Preparation: This was performed by split thickness sharp dissection from the gingival and papillary margins and included muscle/frenum release.
  Root Preparation: This included root planing to remove necrotic cementum and flatten the root surface using curettes and hoes/chisels. Root detoxification was performed using citric acid applied for 1 minute to the root surfaces.
  Graft source: After raising a split thickness flap, the graft was harvested from the right palate and was of medium thickness (1.5-3 mm), approximately 2.0 cm by 5 mm. The harvest site flap was sutured with 5-0 Monofilament.
  Graft Placement: The graft was placed partially on periosteum and partially over root surfaces. Anchor sutures were placed at the base of the graft using 6-0 Braided Vicryl.
  Flap Management: The flap was advanced to completely cover the graft. They were then sutured using 5-0 and 6-0 Braided Vicryl and Nylon using interrupted, sling and continuous mattress suturing.
  Intra-operative Findings: The graft tissue contained glandular and adipose tissue which was removed prior to placing the graft
  Post-operative Status: Bleeding is under control, the patient is comfortable and free of significant pain. Post-op instructions were discussed and dispensed. An analgesic prescription was phoned into the pharmacy.

APPENDIX D

May 21, 2007: Mucogingival Surgery (session title)
CONNECTIVE TISSUE GRAFT #4-5-6 area
Purpose of this procedure:
  To increase connective tissue attachment to the root surface
  To reduce the extent of root exposure that has resulted from mucogingival recession.
Recipient Bed Preparation:
  Performed by split thickness sharp dissection from the gingival and papillary margins
  Included muscle/frenum release.
Root Preparation:
  Root planing to remove necrotic cementum and flatten the root surface using curettes and hoes/chisels.
  Root detoxification using citric acid applied for 1 minute to the root surfaces.
Graft source:
  After raising a split thickness flap, the graft was harvested from the right palate
  It was of medium thickness (1.5-3 mm), approximately 2.0 cm by 5 mm.
  The harvest site flap was sutured with 5-0 Monofilament.
Graft Placement:
  The graft was placed partially on periosteum and partially over root surfaces.
  Anchor sutures were placed at the base of the graft using 6-0 Braided Vicryl.
Flap Management:
  The flap was advanced to completely cover the graft.
  They were then sutured using 5-0 and 6-0 Braided Vicryl and Nylon using interrupted, sling and continuous mattress suturing.
Intra-operative Findings:
  The graft tissue contained glandular and adipose tissue
  The glandular and adipose tissue was removed prior to placing the graft
Post-operative Status:
  Bleeding is under control
  The patient is comfortable and free of significant pain.
  Post-op instructions were discussed and dispensed.
  An analgesic prescription was phoned into the pharmacy.

I claim:

1. A computer based patient clinical records system for dental practices, with the dental practices having a collection of general patient information and a related collection of dental examination and treatment information, said dental patient clinical records system comprising a computer and non-transitory computer readable storage media storing a plurality of non-transitory instructions for enabling operation of said computer, said computer comprising:

a processor accessing the computer readable storage media, the computer readable storage media storing a plurality of non-transitory instructions;

said plurality of non-transitory instructions including:

a. a first plurality of instructions for execution by the computer to obtain a particular patient record from a first collection of general patient information;

b. a second plurality of instructions for execution by the computer to obtain information from a second collection of related dental examination and treatment data are specific to the particular patient;

c. a third plurality of instructions for execution by the computer to display a plurality of windows on a display of the computer, with a first window displaying general patient information of the particular patient, a second window displaying a dental chart, and a third window displaying an editable window having at least one of dental examination information and dental treatment information related to the particular patient, said third window providing an item entry module including a procedure selection plurality of instructions for execution by the computer to specify a procedure and a rules plurality of instructions for execution by the computer to limit user item selection to a plurality of items based on the specified procedure;

d. an anesthesia treatment plurality of instructions stored on the computer readable media, said anesthesia treatment plurality of instructions for execution by the computer to obtain anesthesia treatment information from the user for incorporation into the second collection that are specific to the particular patient;

e. a patient observation plurality of instructions stored on the computer readable media, said patient observation plurality of instructions for execution by the computer to obtain data observed from the particular patient relating to when the patient received the anesthesia treatment and f. an anesthesia record plurality of instructions stored on the computer readable media, said anesthesia record plurality of instructions for execution by the computer to store an anesthesia record in the related collection, the anesthesia record having together both the anesthesia treatment information along with the data observed from the particular patient relating to when the particular patient received the anesthesia treatment, the anesthesia record including stored measurements of blood pressure, pulse, and oxygen saturation of the blood.

2. The system of claim 1 further including a sessions data storage storing a plurality of session entries comprising dental treatment and examination information related to a particular patient session, said storage being accessible to said processor, each said session entry associated with a particular patient from the first general patient information collection and with data in the second collection, wherein the third plurality of instructions populates information in the first, second, and third windows based in part on the dental treatment and examination information stored in a particular one of the session.

3. The system of claim 2 further including a session initiation plurality of instructions stored on the computer readable storage media, the session initiation plurality of instructions for execution by a computer to allow a user to create a new session entry with the new session entry inheriting data from the most recent session entry of a particular patient.

4. The system of claim 2 wherein the sessions data storage is configured to prevent editing of a session entry except for a current session entry.

5. The system of claim 2 further including a form generation plurality of instructions stored on the computer readable storage media, the form generation plurality of instructions for execution by selection of a form from a plurality of category/sub-category forms for user item selection relating to a session entry.

6. The system of claim 5 wherein the form generation plurality of instructions further enables user editing of the plurality of category/sub-category forms.

7. The system of claim 1 wherein said dental examination information includes data on signs of inflammatory activity and plaque with dental and periodontal morphological data pertinent to periodontal evaluation.

8. The system of claim 5 wherein the plurality of category/sub-category forms include categories including at least one of: examinations, procedures, and surgeries.

9. The system of claim 5 wherein the form generation plurality of instructions are configured to provide user item selection screens having at least one of: check boxes, pull-down selections, and free text entry.

10. The system of claim 5 wherein the form generation plurality of instructions further enable creation of documents having text relating to data entered on a form.

11. The system of claim 10 wherein the form generation plurality of instructions further enable creation of at least one of a brief narrative text document, and a comprehensive narrative text document.

12. The system of claim 1 wherein the third plurality of instructions enables editing of information displayed in at least one of the first and second window.

13. The system of claim 1 wherein the second plurality of instructions further enables the computer to obtain prior documents information from the second collection that are specific to the particular patient, and the third plurality of instructions further enables the computer to display a separate window displaying at least one of (a) prior documents related to the particular patient; (b) patient alerts and modifiers information related to the particular patient; (c) general health information related to the particular patient; and (d) medication prescribed information related to the particular patient.

* * * * *